(12) United States Patent
Donen et al.

(10) Patent No.: US 9,187,398 B2
(45) Date of Patent: Nov. 17, 2015

(54) NITRIC ACID OXIDATION PROCESSES

(71) Applicant: Rivertop Renewables, Inc., Missoula, MT (US)

(72) Inventors: Steven Donen, Chanhassen, MN (US); Kirk Hash, Drummond, MT (US); Tyler Smith, Missoula, MT (US); Keith Jensen, Pocatello, ID (US)

(73) Assignee: Rivertop Renewables, Inc., Missoula, MT (US)

( * ) Notice: Subject to any disclaimer, the term of this patent is extended or adjusted under 35 U.S.C. 154(b) by 0 days.

(21) Appl. No.: 14/206,796

(22) Filed: Mar. 12, 2014

(65) Prior Publication Data

US 2014/0275623 A1    Sep. 18, 2014

Related U.S. Application Data

(60) Provisional application No. 61/780,498, filed on Mar. 13, 2013, provisional application No. 61/780,472, filed on Mar. 13, 2013.

(51) Int. Cl.
C07C 51/16   (2006.01)
C07C 51/31   (2006.01)

(52) U.S. Cl.
CPC .................... *C07C 51/316* (2013.01)

(58) Field of Classification Search
CPC .................................... C07C 51/316
USPC ........................................ 562/531
See application file for complete search history.

(56) References Cited

U.S. PATENT DOCUMENTS

| | | |
|---|---|---|
| 1,520,885 A | 12/1924 | Rankin |
| 2,314,831 A | 3/1943 | Kamlet |
| 2,380,196 A | 7/1945 | Solomon |
| 2,419,019 A | 4/1947 | Hales |
| 2,436,659 A | 2/1948 | Mehltretter |
| 2,472,168 A | 6/1949 | Mehltretter |
| 2,529,177 A | 11/1950 | Nieland |
| 2,529,178 A | 11/1950 | Nieland |
| 3,242,207 A | 3/1966 | Ulrich et al. |
| 3,346,623 A | 10/1967 | Young |
| 3,362,885 A | 1/1968 | Harned |
| 3,589,859 A | 6/1971 | Foroulis |
| 3,652,396 A | 3/1972 | Tanaka |
| 3,711,246 A | 1/1973 | Foroulis |
| 3,798,168 A | 3/1974 | Tumerman et al. |
| 3,819,659 A | 6/1974 | Baldwin et al. |
| 3,951,877 A | 4/1976 | Okumura et al. |
| 4,000,083 A | 12/1976 | Heesen |
| 4,108,790 A | 8/1978 | Foroulis |
| 4,120,655 A | 10/1978 | Crambes |
| 4,129,423 A | 12/1978 | Rubin |
| 4,485,100 A | 11/1984 | Hochstrasser et al. |
| 4,512,552 A | 4/1985 | Katayama et al. |
| 4,833,230 A | 5/1989 | Kiely et al. |
| 4,834,793 A | 5/1989 | Schneider et al. |
| 4,845,123 A | 7/1989 | Walaszek |
| 5,017,485 A | 5/1991 | Bringer-Meyer et al. |
| 5,256,294 A | 10/1993 | van Reis |
| 5,264,123 A | 11/1993 | Bailey |
| 5,312,967 A | 5/1994 | Kiely et al. |
| 5,329,044 A | 7/1994 | Kiely et al. |
| 5,330,683 A | 7/1994 | Sufrin |
| 5,364,644 A | 11/1994 | Walaszek |
| 5,376,499 A | 12/1994 | Hammerschmidt et al. |
| 5,434,233 A | 7/1995 | Kiely et al. |
| 5,473,035 A | 12/1995 | Kiely et al. |
| 5,478,374 A | 12/1995 | Kiely |
| 5,531,931 A | 7/1996 | Koefed |
| 5,561,160 A | 10/1996 | Walaszek |
| 5,562,828 A | 10/1996 | Olsen et al. |
| 5,599,977 A | 2/1997 | Kiely et al. |
| 5,891,225 A | 4/1999 | Mishra |
| 5,958,867 A | 9/1999 | Lamberti et al. |
| 5,999,977 A | 12/1999 | Riddle |
| 6,049,004 A | 4/2000 | Kiely et al. |
| 6,156,226 A | 12/2000 | Klyosov et al. |
| 6,372,410 B1 | 4/2002 | Ikemoto et al. |
| 6,498,269 B1 | 12/2002 | Merbough et al. |
| 6,686,325 B2 | 2/2004 | Hoyt et al. |
| 6,831,195 B2 | 12/2004 | Nishimura et al. |
| 6,843,931 B2 | 1/2005 | Sapienza |
| 6,861,009 B1 | 3/2005 | Leist |
| 6,894,135 B2 | 5/2005 | Kiely et al. |
| 6,919,478 B2 | 7/2005 | Kawato et al. |
| 7,125,441 B1 | 10/2006 | Furman et al. |

(Continued)

FOREIGN PATENT DOCUMENTS

| | | |
|---|---|---|
| CA | 2188063 | 4/1998 |
| CN | 1131651 | 9/1996 |

(Continued)

OTHER PUBLICATIONS

U.S. Appl. No. 14/089,054, filed Nov. 25, 2013, Presta.

(Continued)

*Primary Examiner* — Yong Chu
*Assistant Examiner* — Ana Z Muresan
(74) *Attorney, Agent, or Firm* — Lisa V. Mueller; Michael Best & Friedrich LLP

(57) ABSTRACT

A process utilizing nitric acid and oxygen as co-oxidants to oxidize aldehydes, alcohols, polyols, preferably carbohydrates, specifically reducing sugars to produce the corresponding carboxylic acids.

12 Claims, 1 Drawing Sheet

(56) References Cited

U.S. PATENT DOCUMENTS

| | | | |
|---|---|---|---|
| 7,314,906 | B2 | 1/2008 | Kiely et al. |
| 7,658,861 | B2 | 2/2010 | Koefod |
| 7,692,041 | B2 | 4/2010 | Kiely et al. |
| 8,153,573 | B2 | 4/2012 | Miralles et al. |
| 8,623,943 | B2 | 1/2014 | Kiely |
| 8,679,364 | B2 | 3/2014 | Pylkkanen |
| 2003/0109394 | A1 | 6/2003 | Ruhr et al. |
| 2003/0168625 | A1 | 9/2003 | Sapienza et al. |
| 2003/0176305 | A1 | 9/2003 | Hoyt et al. |
| 2004/0025908 | A1 | 2/2004 | Douglas et al. |
| 2004/0028655 | A1 | 2/2004 | Nelson et al. |
| 2004/0185562 | A1 | 9/2004 | Schroeder et al. |
| 2005/0202981 | A1 | 9/2005 | Eveland et al. |
| 2005/0202989 | A1 | 9/2005 | Wilson |
| 2005/0230658 | A1 | 10/2005 | Koefod |
| 2007/0037727 | A1 | 2/2007 | Fiore et al. |
| 2007/0278446 | A1 | 12/2007 | Koefod |
| 2008/0033205 | A1 | 2/2008 | Kiely et al. |
| 2008/0099716 | A1 | 5/2008 | Koefod |
| 2008/0287334 | A1 | 11/2008 | Smith et al. |
| 2008/0302737 | A1 | 12/2008 | Denkewicz, Jr. et al. |
| 2009/0250653 | A1 | 10/2009 | Kiely |
| 2010/0041574 | A1 | 2/2010 | Warkotsch et al. |
| 2010/0130774 | A1 | 5/2010 | Wan et al. |
| 2010/0191002 | A1 | 7/2010 | Kiely |
| 2011/0263905 | A1 | 10/2011 | Purola |
| 2011/0269662 | A1 | 11/2011 | Miralles et al. |
| 2012/0035356 | A1 | 2/2012 | Kiely |
| 2012/0119152 | A1 | 5/2012 | Smith |
| 2012/0277141 | A1 | 11/2012 | Smith |
| 2012/0295986 | A1 | 11/2012 | Smith |
| 2012/0305832 | A1 | 12/2012 | Kiely |

FOREIGN PATENT DOCUMENTS

| | | |
|---|---|---|
| CN | 1970488 | 5/2007 |
| DE | 2016686 | 11/1970 |
| DE | 1929968 | 12/1970 |
| DE | 117492 | 1/1976 |
| DE | 3331751 | 3/1984 |
| DE | 3519884 | 1/1986 |
| EP | 0652305 | 5/1995 |
| EP | 0758678 | 2/1997 |
| EP | 0819653 | 1/1998 |
| EP | 1201617 | 5/2002 |
| FR | 2054945 | 6/1971 |
| FR | 2115300 | 8/1972 |
| GB | 866840 | 5/1961 |
| GB | 2405636 | 9/2003 |
| JP | 47048091 | 12/1972 |
| JP | 551011030 | 1/1976 |
| JP | 51041578 | 11/1976 |
| JP | 54043840 | 4/1979 |
| JP | S57192270 | 11/1982 |
| JP | S58091174 | 5/1983 |
| JP | 60-50188 | 3/1985 |
| JP | S60050188 | 3/1985 |
| JP | 60108352 | 6/1985 |
| JP | 60112676 | 6/1985 |
| JP | 63248782 | 10/1988 |
| JP | 04214057 | 8/1992 |
| JP | H06306652 | 11/1994 |
| JP | H09104687 | 4/1997 |
| JP | 2003306369 | 10/2003 |
| JP | 2004123465 | 4/2004 |
| JP | 2008054806 | 3/2008 |
| KR | 20020066275 | 8/2002 |
| PL | 98149 | 8/1978 |
| RO | 69880 | 4/1981 |
| WO | 92/07108 | 4/1992 |
| WO | WO 00/34221 | 6/2000 |
| WO | WO 2004/052958 | 6/2004 |
| WO | WO 2004/052959 | 6/2004 |
| WO | WO 2008/021054 | 2/2008 |
| WO | WO 2009/065143 | 5/2009 |
| WO | WO 2012/065001 | 5/2012 |
| WO | WO 2012/145688 | 10/2012 |
| WO | WO 2012/145690 | 10/2012 |
| WO | WO 2013/090090 | 6/2013 |

OTHER PUBLICATIONS

Abbadi et al., New Ca-Sequestering Materials Based on the Oxidation of the Hydrolysis Products of Lactose, Green Chem, 1999, 231-235.

Abd El Kader, J.M. et al., "Corrosion inhibition of mild steel by sodium tungstate in neutral solution. Part 3. Coinhibitors and synergism," British Corrosion Journal, 33, 152-157 (1998) Chern Abstr AN 1998:796697.

Abdallah, M. "Sodium gluconate, triethanolamine and their mixtures as corrosion inhibitors of carbon steel in 3.5% NaCl solution," Journal of the Electrochemical Society of India, 48, 121-127, (1999) Chern Abst AN 1999:374923.

Allcock, H.R. et al., "Effect of nonstoichiometric reactant ratios on linear condensation polymers," Contemporary Polymer Chemistry, 2nd Edition, Prentice-Hall, New Jersey (1990) Part II, 274-275.

Billmeyer, F.W., Jr., "Molecular weight and molecular-weight distribution," Textbook of Polymer Science, 3rd Edition, Wiley Interscience, New York (1984) 38-47.

Cantrell, C. E., et al., "s-Dicarbonyl Sugars. 5. A Novel Synthesis of a Branched-Chain Cyclitol," J. Org. Chern. (1977) 42(22):3562-3567.

Carter, Andy, "Modifications in the Preparation of Glucaric Acid and Some 4-alkyl-4-azaheptane-1,7-diamines," 1998, Thesis, University of Alabama, Birmingham, AL, p. 18-20.

Chen, L., "Experimental and Theoretical Studies Concerned with Synthetic Acyclic Carbohydrate Based Polyamides," A Dissertation, University of Alabama at Birmingham (1992).

Chen, L. et al., "Synthesis of steroregular head-tail hydroxylated nylons derived from D-glucose," J. Org. Chem. (1996) 61:5847-5851.

Collepardi, M.M.; "Concrete Admixture Handbook: Properties, Science and Technology", 2nd Edition, Ramachandran,V.S. Editor,Noyes Publications, Park Ridge,NG (1995) p. 286-409.

Cotton, F.A. et al., Advanced Inorganic Chemistry, 1988, p. 341-353, John Wiley and Sons, New York.

CRC Handbook of Chemistry and Physics, edited by Weast et al., 64th Edition, 1983-84, Boca Raton, Florida, p. B-117.

Dorwald, F.Z., Side Reactions in Organic Synthesis. A Guide to Succsesful Synthesis Design, Wiley-VCH Verlag GmbH & Co., Weinheim, Germany (2005) Preface.

Hashimoto et al., "Macromolecular synthesis from caccharic lactones. Ring-opening polyaddition of D-glucaro- and D-mannaro-1,4:6,3-dilactones with alkylenediamines," J. Polym. Sci. Part A: Polym. Chem. (1993) 31:3141-3149.

Hashimoto, K. et al., "Ring-opening polyaddition of D-glucaro-1,4:6,3-dilactone with p-zylylenediamine," Macromol. Chem. Rapid Commun. (1990) 11:393-396.

Haworth et al., "Lactones of mannosaccharic acid, Part I. 2: 5-dimethyl Δ4-manno-saccharo-3: 6-lactone 1-methyl ester, an analogue of ascorbic acid," J. Chem. Soc. London (1944) 56:217-224.

Kiely et al., "Hydroxylated nylons based on unprotected esterified D-glucaric acid by simple condensation reactions," J. Am. Chem. Soc. (1994) 116(2):571-578.

Kirk-Othmer Encyclopedia of Chemical Technology, 3rd Edition, Wiley, New York, vol. 16, 617-634, "Hydrocarbon Resins" to "Hypnotics, Sedatives, Anticonvulsants".

Korzh, E.N. et al., "Acidity and corrosion activity of brine refrigeratnts based on calcium chloride," Zhurnal Prikladnoi Khimii Journal (Russian) (1981) 54:2404-2407, Chern. Abstr. AN 1982-147045.

Lachman, A., "Dihydroxy-Tartaric Acid," Amer. Chern. Soc. (1921) 43:2091-2097.

Lewis, B.A. et al., Chapter 13, "Galactaric acid and its derivatives," Methods in Carbohydrate Chemistry, R.L. Whistler et al., editors, (1953) II:38-46.

(56) References Cited

OTHER PUBLICATIONS

Lin, "Diverse Applications of Carbohydrate Acids in Organic Synthesis," a Dissertation, University of Alabama at Birmingham (1987) p. 48-50, 72-74.
Lowe et al., Soaps and Detergents—The Inorganic Components, J. Am. Oil Chem. Soc., 1978, 55, 32-35.
Mainhardt, H., "N20 Emissions from Adipic Acid and Nitric Acid Production," IPCC Good Practice Guidance and Uncertainty Management in National Greenhouse Gas Inventories (2001).
Marukame, K., S.Fushoku Burnon linkai Shiryo(Nippon Xairyo Gakkai), journal written in Japanese, 173, 1-8, (1993) Chern. Abstr. AN 1993:543767.
Merbough, N. et al., "4-AcNH-tempo-Catalyzed Oxidation of Aldoses to Aldaric Acids Using Chlorine or Bromine as Terminal Oxidants," J. Carbohydr. Chem., 2002, 21:.66-77.
Mor, E. et al., "Steel corrosion inhibition in seawater by calcium organic compounds," Annali deii'University di Ferrara, Sezione 5; Chimica Pura ed Applicata, Journal in French (1971),Chem Abstr AN 1971:414090.
Mor, E. et al., "Zinc gluconate as an inhibitor of the corrosion of mild steel in sea water," Lab Corros. Mar. Met, British Corrosion Journal (1976) 11:199-203 Chern. Abstr. AN 1977:129710.
Mustakas, G.C. et al., "Potassium Acid Saccharate by Nitric Acid Oxidation of Dextrose," Industrial and Engineering Chemistry, Mar. 1954, 427-434.
National Association of Corrosion Engineers (NACE) Standard TM0169-95 as Modified by The Pacific Northwest States, Test Method B, Revision (Apr. 2006).
Ogata, N. et al., "Active polycondensation of diethyl 2,3,4,5-tetrahydroxyadipate with diamines," J. Polym. Sci. Polym. Chem. Ed. (1976) 14:783-792.
Ogata, N. et al., "Copolycondensation of hydroxyl diesters and active diesters with hexamethylenediamine," J. Polym. Sci. Polym. Chem. Ed. (1977) 15:1523-1526.
Ogata, N. et al., "Polycondensation reaction of dimethyl tartrate with hexamethylenediamine in the presence of various matrices," J. Polym. Sci. Polym. Chem. Ed. (1980) 18:939-948.
Ogata, N. et al., "Synthesis of hydrophilic polyamide by active polycondensation," J. Polym. Sci. Polym. Lett. Ed. (1974) 12:355-358.
Ogata, N. et al., "Synthesis of hydrophilic polymide from L-tartarate and diamines by active polycondensation," J. Polym. Sci. Polym. Chem. Ed. (1975) 13:1793-1801.
Ogata, N. et al., "Synthesis of polyamides through active diesters," J. Polym. Sci., Polym. Chem. Ed. (1973) 11:1095-1105.
Ogata, N. et al., "Synthesis of polyesters from active diesters," J. Polym. Sci. Chem. Ed. (1973) 11:2537-2545.
Ogata, N., "New polycondensation systems," Polym. Prepr. (1976) 17:151-156.
Pamuk et al. "The preparation of D-glucaric acid by oxidation of molasses in packed beds" Journal of Chemical Technology and Biotechnology (2001) 76:186-190.
Roper, H., "Selection oxidation of D-glucose: chiral intermediates for industrial utilization," Starch/Starke (1990) 42(9):342-349.
Stanek, J. et al., "Monosaccharide dicarboxylic acids," The Monosaccharides, Academic Press, New York and London (1963) Chapter XXXII, p. 741-752.
Styron, S.D. et al., "MM3(96) conformational analysis of D-glucaramide and x-ray crystal structures of three D-glucaric acid derivatives—models for synthetic poly(alkylene D-glucaramides)," J. Carb. Chem. (2002) 21(1&2):27-51.
Sukhotin,A.M. et al., "Corrosion inhibitor for steel in calcium chloride solutions," Zashchita Mettalov, Journal in Russion (1982) 18:268-70, Chem Ab 1982:476671.
Van Duin et al., Studies on borate esters. Part 8. Interactions of cations with oxyacid anion-bridged esters of D-glucarate in alkaline media, J. Chem. Soc. Dalton Trans., 1987, 8, 2051-2057.
Van Duin et al., Synergic Coordination of Calcium in Borate-Polyhydroxycarboxylate Systems, Carb. Res., 1987, 162, 65-78.

Van Duin, M. et al., "Studies on borate esters. Part 5. The system glucarate borate calcium (II) as studied by 1H, 11B, and 13C nuclear magnetic resonance spectroscopy," J. Chem. Soc. (1987) 2(4):473-478.
Werpy, T. et al., Top Value Added Chemicals from Biomass, Voil-Results of Screening for Potential, www.osti.gov/bridge, U.S. Dept. of Energy, Oak Ridge, TN (2004) 76 pages.
Wilham et al., Organic Acids as Builders in Linear Alkylbenzene Sulfonate Detergent Formulations, J. Am. Oil Chem. Soc., 1971, 48(11), 682-683.
Wisconsin Biorefiners Development Initiative and references therein, Biorefining Processes-Fermentation of 6-Carbon Sugars and Starchs, www.wisbiorefine.org/proc/ferments.pdr (Feb. 5, 2007).
Wrubl, C. et al., "Zinc gluconate as an inhibitor of the corrosion of copper and zinc in seawater," 1st Corros. Mar Met, British Corrosion Journal (1983) 18:142-147, Chem. Abstr. AN 1984:11228.
Yahiro et al., "Efficient acid production from raw corn starch," J. Fermentation Bioengineering (1997) 84(4):375-377.
International Preliminary Report on Patentability for Application No. PCT/US2007/017493 dated Feb. 10, 2009.
International Preliminary Report on Patentability for Application No. PCT/US2008/083831 dated May 18, 2010 (8 pages).
International Preliminary Report on Patentability for Application No. PCT/US2011/060264 dated May 23, 2013 (8 pages).
International Search Report and Written Opinion for Application No. PCT/US2012/034538 dated Jul. 10, 2012 (11 pages).
International Search Report and Written Opinion for Application No. PCT/US2012/034542 dated Jul. 10, 2012 (10 pages).
International Search Report for Application No. PCT/US2003/039733 dated May 13, 2004 (2 pages).
International Search Report for Application No. PCT/US2007/017493 dated Feb. 12, 2008.
International Search Report for Application No. PCT/US2011/060264 dated Feb. 10, 2012.
United States Patent Office Action for U.S. Appl. No. 11/890,760 dated Apr. 16, 2009 (7 pages).
United States Patent Office Action for U.S. Appl. No. 11/890,760 dated Jul. 25, 2008 (8 pages).
United States Patent Office Action for U.S. Appl. No. 12/272,732 dated Apr. 26, 2011.
United States Patent Office Action for U.S. Appl. No. 12/272,732 dated Aug. 24, 2010.
United States Patent Office Action for U.S. Appl. No. 12/272,732 dated Dec. 9, 2011.
United States Patent Office Action for U.S. Appl. No. 12/272,732 dated Jul. 6, 2012 (12 pages).
United States Patent Notice of Allowance for U.S. Appl. No. 12/272,732 dated Aug. 9, 2013 (9 pages).
United States Patent Office Action for U.S. Appl. No. 12/442,135 dated May 16, 2012 (7 pages).
United States Patent Office Action for U.S. Appl. No. 12/442,135 dated Oct. 26, 2011 (7 pages).
United States Patent Office Action for U.S. Appl. No. 12/753,721 dated Dec. 12, 2011 (7 pages).
United States Patent Office Action for U.S. Appl. No. 12/753,721 dated May 9, 2013 (8 pages).
United States Patent Office Notice of Allowance for U.S. Appl. No. 11/890,760 dated Jan. 8, 2010 (6 pages).
United States Patent Office Notice of Allowance for U.S. Appl. No. 12/753,721 dated Aug. 3, 2012 (5 pages).
United States Patent Office Action for U.S. Appl. No. 13/586,953 dated Jul. 1, 2013 (7 pages).
United States Patent Office Action for U.S. Appl. No. 13/586,953 dated Jan. 27, 2014 (7 pages).
United States Patent Office Notice of Allowance for U.S. Appl. No. 13/586,953 dated Aug. 7, 2014 (6 pages).
United States Patent Office Action for U.S. Appl. No. 13/452,560 dated Dec. 4, 2013 (11 pages).
United States Patent Office Action for U.S. Appl. No. 13/452,560 dated Aug. 19, 2014 (10 pages).
United States Patent Office Action for U.S. Appl. No. 13/452,578 dated Sep. 23, 2014 (12 pages).

(56) References Cited

OTHER PUBLICATIONS

United States Patent Office Action for U.S. Appl. No. 14/150,633 dated Sep. 25, 2014 (12 pages).
United States Patent Office Action for U.S. Appl. No. 13/294,085 dated Oct. 3, 2014 (18 pages).
United States Patent Office Action for U.S. Appl. No. 14/205,627 dated Aug. 27, 2014 (25 pages).
United States Patent Office Action for U.S. Appl. No. 14/205,832 dated Aug. 27, 2014 (21 pages).
Copending U.S. Appl. No. 14/205,627, Steven Donen, filed Mar. 12, 2014.
Copending U.S. Appl. No. 14/205,832, Steven Donen, filed Mar. 12, 2014.
Haworth, W.N. et al., "Some derivatives of glucosaccharic acid," J. Chem. Soc. (1944) 65-76.
Mehltretter, C.L. et al., "Sugar Oxidation. Saccharic and oxalic acids by the nitric acid oxidation of dextrose," Agric. and Food Chem. (1953) 1:779-783.
Mehltretter, "D-Glucaric acid," in Methods in Carbohydrate Chemistry, R.L. Whistler eds. Academic Press, New York (1962) vol. II, pp. 46-48.
International Search Report and Written Opinion for Application No. PCT/US2014/024785 dated Jul. 7, 2014 (13 pages).
United States Patent Office Action for U.S. Appl. No. 12/422,135 dated Dec. 17, 2014 (8 pages).
United States Patent Office Action for U.S. Appl. No. 13/294,085 dated Apr. 1, 2015 (15 pages).
United States Patent Office Action for U.S. Appl. No. 14/107,297 dated Mar. 11, 2015 (4 pages).
United States Patent Office Notice of Allowance for U.S. Appl. No. 14/089,054 dated Mar. 2, 2015 (7 pages).
United States Patent Office Action for U.S. Appl. No. 14/727,712 dated Jun. 26, 2015 (14 pages).
United States Patent Office Action for U.S. Appl. No. 14/205,832 dated May 12, 2015 (27 pages).
United States Patent Office Action for U.S. Appl. No. 14/205,627 dated May 15, 2015 (28 pages).
United States Patent Office Notice of Allowance for U.S. Appl. No. 14/150,633 dated Jun. 8, 2015 (9 pages).
United States Patent Office Action for U.S. Appl. No. 14/107,297 dated Jun. 19, 2015 (8 apges).

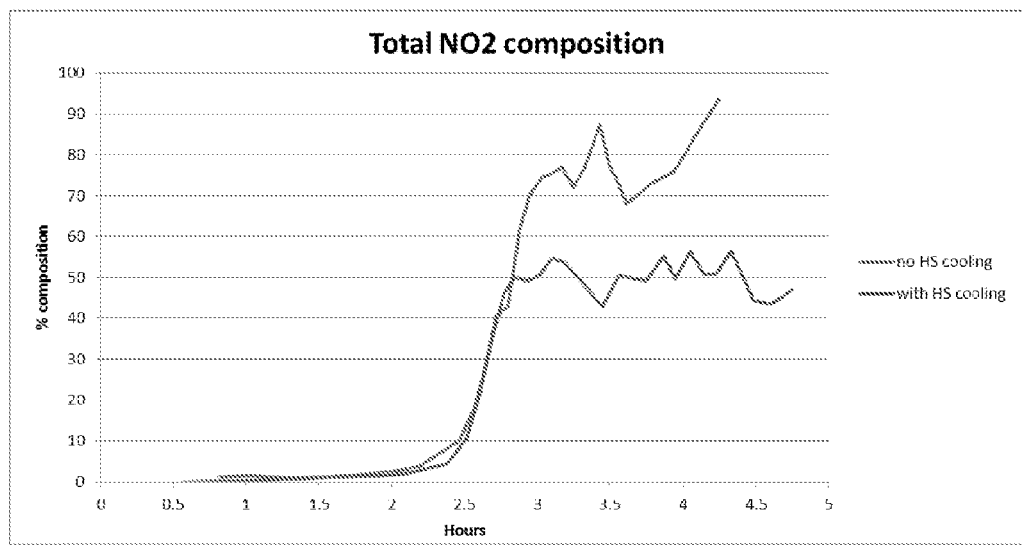

NITRIC ACID OXIDATION PROCESSES

RELATED APPLICATION INFORMATION

This claims priority to U.S. Patent Application No. 61/780,472, filed on Mar. 13, 2013, and U.S. Patent Application No. 61/780,498, filed on Mar. 13, 2013, the entire contents of all of which are fully incorporated herein by reference.

FIELD OF THE INVENTION

This invention describes improved processes utilizing nitric acid and oxygen as co-oxidants to oxidize aldehydes, alcohols and/or polyols, preferably carbohydrates to produce the corresponding carboxylic acids. The improved processes described herein can be used as a batch process or as a continuous process.

BACKGROUND OF THE INVENTION

Hydroxycarboxylic acids, and in particular carbohydrate diacids (aldaric acids) offer significant economic potential as carbon based chemical building blocks for the chemical industry, as safe additives or components of products used in pharmaceutical preparations and food products, and as structural components of biodegradable polymers, if they can be effectively produced on an industrial scale. Glucaric acid, for example, is produced through the oxidation of glucose and in salt form is currently in use as a nutraceutical for preventing cancer. The price of this material however is high, approximately $100/lb. Industrial scale production of aldaric acids would also provide sufficient materials for the production of other useful compounds, that include environmentally degradable polyamides with varying properties and applications, which are otherwise not commercially available.

Carbohydrate diacids are produced a number of ways from reducing sugars using a variety of oxidizing agents, including nitric acid. An example of a nitric acid oxidation of a carbohydrate is that of D-glucose to give D-glucaric acid, typically isolated as its mono potassium salt (See, W. N. Haworth and W. G. M. Jones, J. Chem. Soc., 65-76 (1944), C. L. Mehltretter and C. E. Rist, Agric. and Food Chem., 1, 779-783 (1953) and C. L. Mehltretter, "D-Glucaric Acid", in Methods in Carbohydrate Chemistry, R. L. Whistler, M. L. Wolfrom, Eds; Academic Press, New York, 1962, Vol. II, pp 46-48). Alternatively, D-glucaric acid can be isolated from nitric acid oxidation of D-glucose as a disodium salt (See, D. E. Kiely, A. Carter and D. P. Shrout, U.S. Pat. No. 5,599,977, Feb. 4, 1997) or as the 1,4:6,3-dilactone (See, D. E. Kiely and G. Ponder, U.S. Pat. No. 6,049,004, Apr. 11, 2000). Routes have been described showing synthesis of diacids through catalytic oxidation with oxygen over a noble metal catalyst (See, C. L. Mehltretter, U.S. Pat. No. 2,472,168, Jun. 7, 1949). An additional route of synthesis exists by use of oxoammonium salts in combination with hypohalites as the terminal oxidants. For example, Merbough and coworkers describe oxidation of D-glucose, D-mannose and D-galactose to their corresponding diacids using 4-acetylamino-2,2,4,6-tetamethyl-1-piperidinyloxy (4-AcNH-TEMPO) with hypohalites as the oxidizing medium (See, N. Merbough, J. M. Bobbitt and C. Bruckner, J. Carbohydr. Chem., 21, 66-77 (2002) and Merbouh, J M. Bobbitt, and C. Bruckner, U.S. Pat. No. 6,498,269, Dec. 24, 2002). A microbial oxidation of myo-inositol to glucuronic acid which is then oxidized enzymatically or by catalytic oxidation to glucaric acid has also been recently described (See, W. A. Schroeder, P. M. Hicks, S. McFarlan, and T. W. Abraham, U.S. Patent Application, 20040185562, Sep. 24, 2004).

A variety of different processes for the oxidation of carbohydrates using nitric acid are known. For example, U.S. Pat. No. 2,380,196 (the '196 patent) describes the nitric acid oxidation of carbohydrates to dibasic acids, particularly tartaric acid. The '196 patent describes a cyclic process in which in each cycle, fresh carbohydrate and residue from a previous oxidation is oxidized with nitric acid. A catalyst, such as vanadium, manganese, iron and molybdenum, is employed to increase the yield of tartaric acid. According to the '196 patent, good yields are obtained when the molar ratio of nitric acid to glucose is 5:7.5, preferably 6:7.5. The '196 patent also describes that when mixing the ingredients, the temperature should be maintained at 20° C. or lower. Following mixing, the temperature is raised gradually or allowed to rise spontaneously to about 30° C. to 35° C. (this is the induction or heating-up stage). When the temperature reaches 30° C. to 35° C., an autocatalytic strong exothermic reaction called the "blow" sets in. The "blow" stage is maintained at a temperature of about 50° C. to 75° C., preferably 65-70° C. for anywhere from 45 to 120 minutes. The final temperature stage of the oxidation is the "fume-off" stage at which the last of the nitric acid is reacted and passed off as lower nitrogen oxides. During the "fume-off" stage, the reaction mixture is maintained at a high temperature somewhat below the boiling point of the mixture, at approximately 90° C. to 95° C. until nitrogen oxide is no longer detectable by the fumes. Oxalic and tartaric acids are recovered from the oxidized reaction mixture by direct precipitation and crystallization.

U.S. Pat. No. 2,436,659 (the '659 patent) discloses an improved and economical process for the production of D-saccharic acid. Specifically, the '659 patent discloses a process that produces higher yields of D-saccharic acid in a shorter period of time, is more convenient while not employing the use of metal oxidation catalysts. According to the '659 patent, crystalline D-glucose, in anhydrous or monohydrate form, is added to a solution of nitric acid at a rate that allows control of the temperature of the reaction between 55° C. to 90° C. The mole ratio of glucose to nitric acid used in the process is 1:4. However, the '659 patent notes that a mole ratio of glucose to nitric acid of 1:3 lowers the yield of D-saccharic acid while a ratio of 1:8 increases this yield. The '659 patent also discloses that when 60 to 70 percent nitric acid is used it is preferred to use reaction temperatures of 55° C. to 70° C. and that when lower concentrations of nitric acid are employed higher reaction temperatures are preferred. When the process is performed in this manner, it is quite rapid, with maximum yields of D-saccharic acid being obtained in a one-hour period of oxidation.

U.S. Pat. No. 3,242,207 (the '207 patent) discloses a continuous process for the oxidation of D-glucose with nitric acid at elevated temperatures. Specifically, the process described in the '207 patent is performed as follows: (1) to an initial reaction mixture prepared by oxidizing an aqueous solution of D-glucose with concentrated nitric acids, an aqueous D-glucose solution and concentrated nitric acid in the molecular ratio of 1:3 to 1:3.5 is simultaneously and continuously added at a temperature of about 40° C. to 70° C.; (2) continuously withdrawing from the reaction vessel an apportion of the reaction mixture corresponding to the volume of the fed-in liquids; and (3) isolating the product formed.

U.S. Pat. No. 7,692,041 (the '041 patent) discloses an improved method for oxidizing water soluble compounds using nitric acid oxidation. The method involves (1) preparing an aqueous solution of an organic compound suitable for nitric acid oxidation; (2) combining, over time, employing a controlled process, in a closed reaction vessel, under positive pressure of oxygen, the aqueous solution of the organic compound and an aqueous solution of nitric acid to oxidize the organic compound to a mixture of organic acids; (3) maintaining controlled, moderate temperatures of from about 25° C. to about 50° C., controlled positive pressure of oxygen, and controlled agitation of the organic compound and nitric acid reaction mixture during the oxidation reaction; and (4) removing a portion of the nitric acid from the combined aqueous solution to give a mixture of organic acids suitable for further processing.

There is a need in the art for improved oxidation process that is safe, economical and efficient for converting organic compounds into their corresponding acids.

SUMMARY OF THE INVENTION

In one aspect, the present invention relates to a method of synthesizing a mixture of organic acids, the method comprising the steps of:

(a) combining, over time, in one or more closed reaction vessels, under a positive pressure of oxygen and with continuous mixing, an organic compound suitable for nitric acid oxidation and an aqueous solution of nitric acid to form a first reaction mixture, wherein the organic compound and the aqueous solution of nitric acid are introduced into the one or more closed reaction vessels;

(b) flowing said first reaction mixture through the one or more reaction vessels while maintaining a controlled temperature of from about 5° C. to about 105° C. and controlled positive pressure of oxygen of from about 0 barg to about 1000 barg for a time period suitable to oxidize the organic compound to a subsequent reaction mixture comprising a mixture of organic acid products and nitrogen oxides;

(c) recirculating the subsequent reaction mixture into the reaction vessel vapor space headspace; and (d) recovering nitric acid from the subsequent reaction mixture.

In the above method, the one or more closed reaction vessels comprise one or more reactors. More specifically, the one or more closed reaction vessels are in series (continuous) or in parallel with one another (batch). For example, the reactor can be a continuously stirred tank reactor (CSTRs), falling film reactors or tubular type plug flow reactor almost any type reactor that mixes, controls temperature and pressure and has a liquid and gas phase (not hydraulically full).

The above method can be a continuous process. Alternatively, the above method can be a batch process.

In the above method, the organic compound comprises a single organic material or a mixture of organic materials suitable for nitric acid oxidation.

In another aspect, the above method further comprises the step of removing a significant portion of the nitric acid from the subsequent reaction mixture.

In the above method, the removal of the nitric acid is accomplished by an evaporation, distillation, nanofiltration, diffusion dialysis or alcohol or ether precipitation.

The above method further comprises the step of making basic the subsequent reaction mixture from which most of the nitric acid has been removed to convert residual nitric acid to inorganic nitrate and the mixture of organic acids to a mixture of organic acid salts.

In the above method, organic compound suitable for nitric acid oxidation is selected from the group consisting of monohydric alcohols, diols, polyols, aldehydes, ketones, carbohydrates, hydroxyacids, cellulose, starch and combinations thereof. For example, the carbohydrates are selected from the group consisting of monosaccharides, disaccharides, oligosaccharides, aldonic acids, aldonic acid esters, aldonic acid salts, aluronic acids, alduronic acid esters, alduronic acid salts, alditols, cyclitols, corn syrups with different dextrose equivalent values, and monosaccharides, disaccharides, oligosaccharides and polysaccharides derived from plants, microorganisms or biomass sources.

In the above method, the nitrogen oxides are $N_2O_3$, $N_2O_4$, NO, $NO_2$ and $N_2O$.

In another aspect, the present invention relates to a method of synthesizing a mixture of organic acids, the method comprising the steps of:

(a) combining, over time, in one or more closed reaction vessels, under a positive pressure of oxygen and with continuous stirring mixing an organic compound suitable for nitric acid oxidation and an aqueous solution of nitric acid to form a reaction mixture, wherein the organic compound and the aqueous solution of nitric acid are concurrently introduced into the one or more closed reaction vessels;

(b) flowing said reaction mixture through the one or more closed reaction vessels while (i) maintaining a controlled temperature of from about 5° C. to about 105° C. in a portion of the reaction vessel, (ii) maintaining a reaction vessel headspace temperature of from about 80° C. to about −42° C.; and (iii) a controlled positive pressure of oxygen of from about 0 barg to about 1000 barg for a time period suitable to oxidize the organic compound to a subsequent reaction mixture comprising a mixture of organic acid products and nitrogen oxides; and (c) removing most of nitric acid from the subsequent reaction mixture to give a final reaction mixture of organic acids suitable for further processing.

In the above method, the one or more closed reaction vessels comprise one or more reactors. More specifically, the one or more closed reaction vessels are in series (continuous) or in parallel with one another (batch). For example, the reactor can be a continuously stirred tank reactor (CSTRs), falling film reactor or a tubular type plug flow reactor or almost any type reactor that can mix, controls temperature and pressure and has a liquid and gas phase (not hydraulicly full). The above method can be a continuous process. Alternatively, the above method can be a batch process.

In the above method, the organic compound comprises a single organic material or a mixture of organic materials suitable for nitric acid oxidation.

In another aspect, the above method further comprises the step of removing a significant portion of the nitric acid from the subsequent reaction mixture.

In the above method, the removal of the nitric acid is accomplished by an evaporation, distillation, nanofiltration, diffusion dialysis or alcohol or ether precipitation.

The above method further comprises the step of making basic the subsequent reaction mixture from which most of the nitric acid has been removed to convert residual nitric acid to inorganic nitrate and the mixture of organic acids to a mixture of organic acid salts.

In the above method, organic compound suitable for nitric acid oxidation is selected from the group consisting of monohydric alcohols, diols, polyols, aldehydes, ketones, carbohydrates, hydroxyacids, cellulose, starch and combinations thereof. For example, the carbohydrates are selected from the group consisting of monosaccharides, disaccharides, oligosaccharides, aldonic acids, aldonic acid esters, aldonic acid salts, aluronic acids, alduronic acid esters, alduronic acid salts, alditols, cyclitols, corn syrups with different dextrose equivalent values, and monosaccharides, disaccharides, oligosaccharides and polysaccharides derived from plants, microorganisms or biomass sources.

In the above method, the nitrogen oxides are $N_2O_3$, $N_2O_4$, NO, $NO_2$ and $N_2O$.

BRIEF DESCRIPTION OF THE FIGURE

FIG. 1 provides the results described in Example 11 demonstrating a lower $NO_2$ composition in the headspace of a reactor equipped with headspace cooling compared to that of an identical reactor not equipped with headspace cooling.

DETAILED DESCRIPTION OF THE INVENTION

The present invention relates to a safe, efficient and economical oxidation process for oxidizing organic compounds into their corresponding organic acid products. Specifically, this invention relates to an improved method for regenerating nitric acid in situ during the oxidation reaction while also improving the safety and quality of the final product. Effective regeneration of nitric acid reduces the amount of nitric acid required to accomplish the oxidation and allows subsequent recovery and recycling of the nitric acid thus improving the efficiency and economy of the process. However, increasing the amount of nitric acid during the reaction can also lead to run away oxidation rates and over oxidation of the organic substrate. Other patents have disclosed methods for regenerating nitric acid in situ during the oxidation process. U.S. Pat. No. 7,692,041 (the '041 patent) discloses an improved method for oxidizing water soluble compounds using nitric acid oxidation whereby a positive pressure of oxygen is introduced during the reaction to convert gaseous oxides of nitrogen (NOx), by-products from the oxidation, back to nitric acid. The process described in the '041 patent uses a sealed vessel, pressurized with oxygen to re-oxidize NOx in the headspace back to nitric acid, thereby improving reaction rates by increasing the nitric acid concentration in the liquid reaction phase. The '041 patent does not describe alternative methods of improving nitric acid regeneration or oxidation reaction rates. One skilled in the art would expect that increasing the temperature in the headspace would improve nitric acid regeneration by increasing the oxidation rate of NOx back to nitric acid. One skilled in the art would also expect that improving mass transfer of the gas phase back into the liquid phase would increase oxidation rates of the organic substrate.

To better understand the effects of headspace temperature, the inventors used a reactor capable of independently heating and cooling gas and liquid. The '041 patent does not disclose using a reactor having a separate control over headspace and liquid temperatures. Surprisingly, the inventors found that cooling, instead of heating, the headspace below the temperature of the liquid phase improved the overall rate of nitric acid regeneration. Increasing the rate of nitric acid regeneration allows the oxidation process of this invention to use less nitric acid than previously described to achieve the same degree of oxidation.

Additionally, in another aspect, while trying to improve nitric acid regeneration by increasing mass transfer of the gas phase into the liquid phase by recirculating the liquid reaction mixture into the gaseous headspace, the inventors surprisingly discovered that the oxidation reaction rates did not increase and in fact, the oxidation was quenched and conversion of the organic substrate into organic acid products was stopped. This surprising result may be used to control the energetic oxidation reaction, particularly in preventing over oxidation of the organic substrate once the desired level of oxidation has been reached. This is particularly effective when combined with improved nitric acid regeneration through cooling of the headspace which leads to faster oxidation rates and makes control over the degree of oxidation difficult to control.

The oxidation process described herein can be performed as a batch-type process or as a continuous process. The first step of the process of the present invention involves combining an organic compound suitable for nitric acid oxidation with an aqueous solution of nitric acid to form an initial or first reaction mixture, whereby the organic compound is oxidized to form a reaction mixture of organic acids (which constitute part of the liquid phase during the reaction). It should also be noted that during the oxidation that gaseous oxides of nitrogen (gaseous oxides of nitrogen are also referred to herein as "nitrogen oxides" and include $N_2O_3$, $N_2O_4$, NO, $NO_2$ and $N_2O$) are produced in the reaction mixture (which constitute part of the gas or gaseous phase). In one aspect, the organic compound and aqueous solution of nitric acid can be injected simultaneously or sequentially, in any order, into one or more closed reaction vessels that comprise a reaction vessel train.

The organic compounds that can be used in the process of the present invention can generally be described to include monohydric alcohols, diols, polyols, aldehydes, ketones, carbohydrates, and mixtures thereof. Non-limiting examples of carbohydrates that may be used in the processes of the current invention include, but are not limited to, monosaccharides, such as the common monosaccharides D-glucose, D-mannose, D-xylose, L-arabinose, D-arabinose, D-galactose, D-arabinose, D-ribose, D-fructose; disaccharides, such as the common disaccharides maltose, sucrose, isomaltose, cellobiose and lactose; oligosaccharides, for example, maltotriose and maltotetrose; aldonic acids such as D-gluconic acid, D-ribonic acid, and D-galactonic acid; aldonic acid esters, lactones and salts that include, but are not limited to, those derived from D-gluconic acid, D-ribonic acid and D-galactonic acid; alduronic acids, for example, D-glucuronic acid and L-iduronic acid; alduronic esters, lactones and salts that include, but are not limited to, those derived from D-glucuronic acid and L-iduronic acid; alditols that include glycerol, threitol, erythritol, xylitol, D-glucitol; alditols with more than six carbon atoms; cyclitols, for example common cyclitols such as myo-inositol and scyllitol; corn syrups with different dextrose equivalent values; other aldonic acids and salts thereof, such as, glucoheptonic acids, glycerbionic acids, erythrobionic acids, threobionic acids, ribobionic acids, arabinobionic acids, xylobionic acids, lyxobionic acids, allobionic acids, altrobionic acids, glucobionic acids, mannobionic acids, gulobionic acids, idobionic acids, galactobionic acids, talobionic acids, alloheptobionic acids, altroheptobionic acids, glucoheptobionic acids, mannoheptobionic acids, guloheptobionic acids, idoheptobionic acids, galactoheptobionic acids and taloheptobionic acids; glycols such as ethylene glycol, diethylene glycols, triethylene glycols or mixtures thereof; mixtures of carbohydrates from different biomass, plant or microorganism sources; polysaccharides from biomass, plant or microorganism sources (such as starch, celluloses, etc.) and of varying structures, saccharide units and molecular weights. The organic compound may also comprise a combination of one or more of the organic compounds. The organic compound may be added neat (namely, as pure substance as a solid or liquid (namely, aqueous)), depending on the desired properties of the reaction mixture. In one aspect, the organic compound is provided as an aqueous solution.

As mentioned previously herein, the organic compound is combined with an aqueous solution of nitric acid to form the initial or first reaction mixture. The concentration of nitric acid used in the process of the present invention is not critical. For example, the nitric acid used can be 60% nitric acid, 70% nitric acid, etc. It will be understood by one skilled in the art that the ratio of aqueous nitric acid to organic compound used in the process of the present invention can vary depending on the desired oxidation product composition. The molar ratio is calculated at the beginning of the reaction if all reactants are added at the beginning of the reaction in batch (all together) or in a continuous flow reactor system (all together in the first reactor of the reactor system). The molar ratio is calculated at the end of the reaction step if a fed batch is used (the phrase "fed batch" means starting with one of the reactants (such as an organic compound or nitric acid) in a reaction vessel and then adding the other reactants as the reaction progresses to completion) or if a continuous series of reaction vessels are used and one of the reactants is added at different locations through the reactor train (an amount is added to each reactor vessel in the reactor train). In one aspect, the molar ratio of aqueous nitric acid to organic compound ranges from approximately 0.1:1 to approximately 2:1. In yet another aspect, the molar ratio of aqueous nitric acid to organic compound ranges from approximately 0.25:1 to approximately 1.8:1. In still yet another aspect, the molar ratio of aqueous nitric acid to organic compound ranges from approximately 0.25:1 to approximately 1.7:1. In still yet another aspect, the molar ratio of aqueous nitric acid to organic compound ranges from approximately 0.25:1 to approximately 1.6:1. In still yet another aspect, the molar ratio of aqueous nitric acid to organic compound ranges from approximately 0.25:1 to approximately 1.5:1. In yet another aspect, the molar ratio of aqueous nitric acid to organic compound ranges from approximately 0.25:1 to approximately 1.4:1. In yet another aspect, the molar ratio of aqueous nitric acid to organic compound ranges from approximately 0.25:1 to approximately 1.3:1. In yet another aspect, the molar ratio of aqueous nitric acid to organic compound ranges from approximately 0.25:1 to approximately 1.2:1. In yet another aspect, the molar ratio of aqueous nitric acid to organic compound ranges from approximately 0.25:1 to approximately 1:1. In yet another aspect, the molar ratio of aqueous nitric acid to organic compound is approximately 0.25:1 to approximately 0.9:1. In yet another aspect, the molar ratio of aqueous nitric acid to organic compound is approximately 0.25:1 to approximately 0.8:1. In yet another aspect, the molar ratio of aqueous nitric acid to organic compound is approximately 0.25:1 to approximately 0.75:1. In yet another aspect, the molar ratio of aqueous nitric acid to organic compound is approximately 0.25:1 to approximately 0.65:1. In yet another aspect, the molar ratio of aqueous nitric acid to organic compound ranges from approximately 0.4:1 to approximately 1.8:1. In yet another aspect, the molar ratio of aqueous nitric acid to organic compound ranges from approximately 0.4:1 to approximately 1.7:1. In yet another aspect, the molar ratio of aqueous nitric acid to organic compound ranges from approximately 0.4:1 to approximately 1.6:1. In yet another aspect, the molar ratio of aqueous nitric acid to organic compound ranges from approximately 0.4:1 to approximately 1.5:1. In yet another aspect, the molar ratio of aqueous nitric acid to organic compound ranges from approximately 0.4:1 to approximately 1.4:1. In yet another aspect, the molar ratio of aqueous nitric acid to organic compound ranges from approximately 0.4:1 to approximately 1.3:1. In yet another aspect, the molar ratio of aqueous nitric acid to organic compound ranges from approximately 0.4:1 to approximately 1.2:1. In yet another aspect, the molar ratio of aqueous nitric acid to organic compound ranges from approximately 0.4:1 to approximately 1:1. In another aspect, the molar ratio of aqueous nitric acid to organic compound is approximately 0.4:1 to approximately 0.9:1. In another aspect, the molar ratio of aqueous nitric acid to organic compound is approximately 0.4:1 to approximately 0.8:1. In another aspect, the molar ratio of aqueous nitric acid to organic compound is approximately 0.4:1 to approximately 0.75:1. In another aspect, the molar ratio of aqueous nitric acid to organic compound is approximately 0.4:1 to approximately 0.65:1. In yet another aspect, the molar ratio of aqueous nitric acid to organic compound ranges from approximately 0.5:1 to approximately 1.8:1. In yet another aspect, the molar ratio of aqueous nitric acid to organic compound ranges from approximately 0.5:1 to approximately 1.7:1. In yet another aspect, the molar ratio of aqueous nitric acid to organic compound ranges from approximately 0.5:1 to approximately 1.6:1. In yet another aspect, the molar ratio of aqueous nitric acid to organic compound ranges from approximately 0.5:1 to approximately 1.5:1. In yet another aspect, the molar ratio of aqueous nitric acid to organic compound ranges from approximately 0.5:1 to approximately 1.4:1. In yet another aspect, the molar ratio of aqueous nitric acid to organic compound ranges from approximately 0.5:1 to approximately 1.3:1. In yet another aspect, the molar ratio of aqueous nitric acid to organic compound ranges from approximately 0.5:1 to approximately 1.2:1. In yet another aspect, the molar ratio of aqueous nitric acid to organic compound ranges from approximately 0.5:1 to approximately 1:1. In another aspect, the molar ratio of aqueous nitric acid to organic compound is approximately 0.5:1 to approximately 0.9:1. In another aspect, the molar ratio of aqueous nitric acid to organic compound is approximately 0.5:1 to approximately 0.8:1. In another aspect, the molar ratio of aqueous nitric acid to organic compound is approximately 0.5:1 to approximately 0.75:1. In another aspect, the molar ratio of aqueous nitric acid to organic compound is approximately 0.5:1 to approximately 0.65:1. In another aspect, the molar ratio of aqueous nitric acid to organic compound is approximately 0.5:1 to approximately 0.65:1. In a further aspect, the molar ratio of aqueous nitric acid to organic compound is approximately 0.5:1. In a further aspect, the molar ratio of aqueous nitric acid to organic compound is approximately 0.6:1. In a further aspect, the molar ratio of aqueous nitric acid to organic compound is approximately 0.7:1. In a further aspect, the molar ratio of aqueous nitric acid to organic compound is approximately 0.8:1. In a further aspect, the molar ratio of aqueous nitric acid to organic compound is approximately 0.9:1. In yet a further aspect, the molar ratio of aqueous nitric acid to organic compound is approximately 0.1:2. In still yet a further aspect, the molar ratio of aqueous nitric acid to organic compound is approximately 0.1:1.5. In still yet a further aspect, the molar ratio of aqueous nitric acid to organic compound is approximately 0.1:1. In yet a further aspect, the molar ratio of aqueous nitric acid to organic compound is approximately 0.25:3. In still yet a further aspect, the molar ratio of aqueous nitric acid to organic compound is approximately 0.25:1.5. In still yet a further aspect, the molar ratio of aqueous nitric acid to organic compound is approximately 0.25:1. In yet a further aspect, the molar ratio of aqueous nitric acid to organic compound is approximately 0.50:2. In still yet a further aspect, the molar ratio of aqueous nitric acid to organic compound is approximately 0.50:1.5. In still yet another aspect, the molar ratio of aqueous nitric acid to organic compound is approximately 1.5:1. In still yet another aspect, the molar ratio of aqueous nitric acid to organic compound is approximately 2:1.

Optionally, inorganic nitrate can be added into the reaction mixture at any time during the oxidation process. Generally, the inorganic nitrite will be added at the beginning during the period of time that the first reaction mixture is being formed. Generally, once the oxidation reaction has begun, it may no longer be necessary to add any additional nitrate.

The initial reaction mixture is prepared (in one or more reaction vessels) at a temperature that generally ranges from about 5° C. to about 105° C. For example, the temperature ranges may be from about 10° C. to about 105° C., about 15° C. to about 105° C., about 20° C. to about 105° C., about 25° C. to about 105° C., about 30° C. to about 105° C., about 35° C. to about 105° C., about 40° C. to about 105° C., about 45° C. to about 105° C., about 50° C. to about 105° C., about 55° C. to about 105° C., about 60° C. to about 105° C., about 5° C. to about 100° C., about 10° C. to about 100° C., about 15° C. to about 100° C., about 20° C. to about 100° C., about 25° C. to about 100° C., about 30° C. to about 100° C., about 35° C. to about 100° C., about 40° C. to about 100° C., about 45° C. to about 100° C., about 50° C. to about 100° C., about 55° C. to about 100° C., about 60° C. to about 100° C., about 5° C. to about 95° C., about 10° C. to about 95° C., about 15° C. to about 95° C., about 20° C. to about 95° C., about 25° C. to about 95° C., about 30° C. to about 95° C., about 35° C. to about 95° C., about 40° C. to about 95° C., about 45° C. to about 95° C., about 50° C. to about 95° C., about 55° C. to about 95° C., about 60° C. to about 95° C., about 5° C. to about 90° C., about 10° C. to about 90° C., about 15° C. to about 90° C., about 20° C. to about 90° C., about 25° C. to about 90° C., about 30° C. to about 90° C., about 35° C. to about 90° C., about 40° C. to about 90° C., about 45° C. to about 90° C., about 50° C. to about 90° C., about 55° C. to about 90° C., about 60° C. to about 90° C., about 5° C. to about 85° C., about 10° C. to about 85° C., about 15° C. to about 85° C., about 20° C. to about 85° C., about 25° C. to about 85° C., about 30° C. to about 85° C., about 35° C. to about 85° C., about 40° C. to about 85° C., about 45° C. to about 85° C., about 50° C. to about 85° C., about 55° C. to about 85° C., about 60° C. to about 85° C., about 5° C. to about 80° C., about 10° C. to about 80° C., about 15° C. to about 80° C., about 20° C. to about 80° C., about 25° C. to about 80° C., about 30° C. to about 80° C., about 35° C. to about 80° C., about 40° C. to about 80° C., about 45° C. to about 80° C., about 50° C. to about 80° C., about 55° C. to about 80° C., about 60° C. to about 80° C., about 5° C. to about 70° C., about 10° C. to about 70° C., about 15° C. to about 70° C., about 20° C. to about 70° C., about 25° C. to about 70° C., about 30° C. to about 70° C., about 35° C. to about 70° C., about 40° C. to about 70° C., about 45° C. to about 70° C., about 50° C. to about 70° C., about 55° C. to about 70° C., about 60° C. to about 70° C., about 55° C. to about 105° C., about 60° C. to about 105° C., about 65° C. to about 105° C., about 70° C. to about 105° C., about 75° C. to about 105° C., about 80° C. to about 105° C., about 85° C. to about 105° C., about 90° C. to about 105° C., about 55° C. to about 100° C., about 60° C. to about 100° C., about 65° C. to about 100° C., about 70° C. to about 100° C., about 75° C. to about 100° C., about 80° C. to about 100° C., about 85° C. to about 100° C., about 90° C. to about 100° C., about 55° C. to about 95° C., about 60° C. to about 95° C., about 65° C. to about 95° C., about 70° C. to about 95° C., about 75° C. to about 95° C., about 80° C. to about 95° C., about 85° C. to about 95° C., about 90° C. to about 95° C., about 55° C. to about 90° C., about 60° C. to about 90° C., about 65° C. to about 90° C., about 70° C. to about 90° C., about 75° C. to about 90° C., about 80° C. to about 90° C., about 85° C. to about 90° C., about 10° C. to about 55° C., about 15° C. to about 55° C., about 20° C. to about 55° C., about 25° C. to about 55° C., about 10° C. to about 50° C., about 15° C. to about 50° C., about 20° C. to about 50° C., about 25° C. to about 50° C., about 10° C. to about 45° C., about 15° C. to about 45° C., about 20° C. to about 45° C., about 25° C. to about 45° C., about 10° C. to about 40° C., about 15° C. to about 40° C., about 20° C. to about 40° C., about 25° C. to about 40° C., about 10° C. to about 35° C., about 15° C. to about 35° C., about 20° C. to about 35° C., about 25° C. to about 35° C., about 10° C. to about 30° C., about 15° C. to about 30° C., about 20° C. to about 30° C., or about 25° C. to about 30° C.

As mentioned previously, the reaction mixture is contained within one or more closed reaction vessels that are capable of carrying out the oxidation process. For example, any type of reaction vessel that allows for the gas and liquid phases to have a high mass transfer during the oxidation reaction can be used. In one aspect, the reactor is capable of independently heating and cooling the gas and liquid phases. Examples of reactor vessels that can be used include one or more continuously stirred tank reactors (CSTRs), plug flow reactors, spinning disc reactors, or tubular type plug flow reactors. Additionally, the reaction vessel can contain heat transfer systems such as coils, jackets, loops, etc. Furthermore, when one or more reaction vessels are used, any combination of different types and kinds of reaction vessels can be use. For example, the reaction train can contain a combination of one or more CSTRs, one or more tubular type plug flow reactors, and/or one or more evaporators. The reaction train contain one reaction vessel, two reaction vessels, three reaction vessels, four reaction vessels, five reaction vessels, six reaction vessels, seven reaction vessels, eight reaction vessels, nine reaction vessels or ten reaction vessels. If one or more reaction vessels are used, the reaction vessels can be connected in series with one another or one (such as in a continuous process) or one or more reaction vessels can be used in parallel (such as in a batch process).

The reaction vessel can be described as a container or vessel that is insulated from the external environment, such that the reaction mixture contained within the tank reactor is not exposed to ambient air. Additionally, the reaction vessel can comprise one or more mixing elements that are capable of continuously stirring and providing controlled agitation of the reaction mixture within the vessel. The one or more mixing elements may include, but are not limited to magnetic stirrers, propeller stirrers, turbine stirrers, anchor stirrers, kneading stirrers, centrifugal stirrers, paddle stirrers and combinations thereof. Generally, the mixing element is electronically controlled such that the spinning velocity of the mixing element may be altered as needed.

The reaction vessel typically maintains a vapor or head space wherein the gaseous phase (gaseous oxides of nitrogen) exists in addition to the liquid phase. The vapor or head space is created by filing the tank reactor with a volume of the reaction mixture that is less than 100% of the volume of the tank. Generally, the reaction vessel is filled with a volume that ranges from approximately 1% of the reaction vessel volume to approximately 99% of the reaction vessel volume. In certain aspects of the current invention, the reaction mixture comprises a volume of the reaction vessel that is not greater than 95%, not greater than 90%, not greater than 85%, not greater than 80%, not greater than 75%, not greater than 70%, not greater than 65%, not greater than 60%, not greater than 55%, not greater than 50%, not greater than 45%, not greater than 40%, not greater than 35%, not greater than 30%, not greater than 25%, not greater than 20%, not greater than 15%, not greater than 10%, and not greater than 5%.

In one aspect, the vapor or head space of one or more reaction vessels may be maintained at a temperature of from about 80° C. to about −42° C. For example, the temperature of the vapor (gas phase) or head space can be from about 80° C. to about −41° C., about 80° C. to about −40° C., about 80° C. to about −35° C., about 80° C. to about −30° C., about 80° C. to about −20° C., about 80° C. to about −15° C., about 80° C. to about −10° C., about 80° C. to about 0° C., about 80° C. to about 10° C., about 80° C. to about 20° C., about 80° C. to about 30° C., about 80° C. to about 40° C., about 70° C. to about −42° C., about 70° C. to about −41° C., about 70° C. to about −40° C., about 70° C. to about −35° C., about 70° C. to about −30° C., about 70° C. to about −20° C., about 70° C. to about −15° C., about 70° C. to about −10° C., about 70° C. to about 0° C., about 70° C. to about 10° C., about 70° C. to about 20° C., about 70° C. to about 30° C., about 70° C. to about 40° C., about 60° C. to about −42° C., about 60° C. to about −41° C., about 60° C. to about −40° C., about 60° C. to about −35° C., about 60° C. to about −30° C., about 60° C. to about −20° C., about 60° C. to about −15° C., about 60° C. to about −10° C., about 60° C. to about 0° C., about 60° C. to about 10° C., about 60° C. to about 20° C., about 60° C. to about 60° C., about 60° C. to about 40° C., about 50° C. to about −42° C., about 50° C. to about −41° C., about 50° C. to about −40° C., about 50° C. to about −35° C., about 50° C. to about −30° C., about 50° C. to about −20° C., about 50° C. to about −15° C., about 50° C. to about −10° C., about 50° C. to about 0° C., about 50° C. to about 10° C., about 50° C. to about 20° C., about 50° C. to about 30° C., about 50° C. to about 40° C., about 40° C. to about −42° C., about 40° C. to about −41° C., about 40° C. to about −40° C., about 40° C. to about −35° C., about 40° C. to about −30° C., about 40° C. to about −20° C., about 40° C. to about −15° C., about 40° C. to about −10° C., about 40° C. to about 0° C., about 40° C. to about 10° C., about 40° C. to about 20° C., about 40° C. to about 30° C., about 30° C. to about −42° C., about 30° C. to about −41° C., about 30° C. to about −40° C., about 30° C. to about −35° C., about 30° C. to about −30° C., about 30° C. to about −20° C., about 30° C. to about −15° C., about 30° C. to about −10° C., about 30° C. to about 0° C., about 30° C. to about 10° C., about 30° C. to about 20° C., about 20° C. to about −42° C., about 20° C. to about −41° C., about 20° C. to about −40° C., about 20° C. to about −35° C., about 20° C. to about −30° C., about 20° C. to about −20° C., about 20° C. to about −15° C., about 20° C. to about −10° C., about 20° C. to about 0° C., about 20° C. to about 10° C., about 10° C. to about −42° C., about 10° C. to about −41° C., about 10° C. to about −40° C., about 10° C. to about −35° C., about 10° C. to about −30° C., about 10° C. to about −20° C., about 10° C. to about −15° C., about 10° C. to about −10° C., about 10° C. to about 0° C., about 5° C. to about −42° C., about 5° C. to about −41° C., about 5° C. to about −40° C., about 5° C. to about −35° C., about 5° C. to about −30° C., about 5° C. to about −20° C., about 5° C. to about −15° C., about 5° C. to about −10° C. or about 5° C. to about 0° C. While the vapor or head space of one or more reaction vessels may be maintained at a temperature of from about 80° C. to about −42° C., the liquid phase of the one or more reaction vessels may be maintained at a temperature of 5° C. to about 105° C. In one aspect, the vapor or head space is maintained at a lower temperature than the temperature of the liquid phase in the reaction vessel. For example, the vapor or head space is at least 1° C., 5° C., 10° C., 15° C., 20° C., 25° C., 30° C., 35° C., 40° C., 45° C., 50° C., 55° C., 60° C., 65° C., 70° C., 75° C., 80° C., 85° C., 90° C., 95° C. or 100° C. cooler than the liquid phase.

By specifically controlling the head space temperature and pressure, the inventors of the present invention found that this results in an improvement in the rate of conversion of nitrogen oxides to nitric acid in the vapor space. Specifically, the inventors found that cooling the headspace below the temperature of the liquid phase improved (namely, increased) the overall rate of nitric acid regeneration (as evidence by a reduction in the number of units of nitrogen oxides (such as $NO_2$) generated in the headspace. Increasing the rate of nitric acid regeneration allows the oxidation process in this invention to use less nitric acid than previously described to achieve the same degree of oxidation. In addition, the process of the present invention is more economical because less nitric acid is lost during pressure control venting of the reaction and during the recovery steps of the process discussed later herein. In other words, the method of the present invention results in a "low waste" oxidation process which has not existed previously. As used herein, the term "low waste" means that less than 1%, less than 0.9%, less than 0.8%, less than 0.7%, less than 0.6%, less than 0.5%, less than 0.4%, less than 0.3%, less than 0.2%, less than 0.1% of nitric acid is lost during the process of the present invention during pressure control venting of the reaction and during the recovery steps. Additionally, controlling the headspace temperature as described herein results in the reaction vessel having to be vented less frequently or not at all during the oxidation process, specifically when compared with process that does not control the headspace temperature as described herein.

The process of the present invention requires exposing the first reaction mixture to the positive pressure of oxygen. Therefore, oxygen is added at point at time and at some location in the one or more reaction vessels. The addition of oxygen and the location of its addition may be during the formation of the initial or first reaction mixture. Alternatively, in another aspect, oxygen can be added in the last reactor or only reactor (if only a single reactor comprises the reaction train). Still further alternatively, oxygen may be added at a selected reactor in the reaction vessel train. Still further alternatively, oxygen can be to each individual reaction vessel comprising the reaction vessel train. The oxygen may be introduced into the first reaction mixture by any means known in the art, including bubbling gaseous oxygen through the reaction mixture. The oxygen added to the reaction vessel train can be added cocurrently or countercurrently or both cocurrently and countercurrently. The pressure within the reaction vessel generally ranges from above about 0 barg to about 1000 barg. In one aspect, the pressure can range from about 1 barg to about 1000 barg, about 5 barg to about 1000 barg, about 10 barg to about 1000 barg, 20 barg to about 1000 barg, about 30 barg to about 1000 barg, about 40 barg to about 1000 barg, 50 barg to about 1000 barg, about 60 barg to about 1000 barg, about 70 barg to about 1000 barg, about 80 barg to about 1000 barg, about 90 barg to about 1000 barg, about 100 barg to about 1000 barg, about 200 barg to about 1000 barg, about 300 barg to about 1000 barg, about 400 barg to about 1000 barg, about 50 barg to about 1000 barg, 0 barg to about 900 barg, 1 barg to about 900 barg, about 5 barg to about 900 barg, about 10 barg to about 900 barg, 20 barg to about 900 barg, about 30 barg to about 900 barg, about 40 barg to about 900 barg, 50 barg to about 900 barg, about 60 barg to about 900 barg, about 70 barg to about 900 barg, about 80 barg to about 900 barg, about 90 barg to about 900 barg, about 100 barg to about 900 barg, about 200 barg to about 900 barg, about 300 barg to about 900 barg, about 400 barg to about 900 barg, about 50 barg to about 900 barg, 0 barg to about 800 barg, 1 barg to about 800 barg, about 5 barg to about 800 barg, about 10 barg to about 800 barg, 20 barg to about 800 barg, about 30 barg to about 800 barg, about 40 barg to about 800 barg, 50 barg to about 800 barg, about 60 barg to about 800 barg, about 70 barg to about 800 barg, about 80 barg to about 800 barg, about 90 barg to about 800 barg, about 100 barg to about 800 barg, about 200 barg to about 800 barg, about 300 barg to about 800 barg, about 400 barg to about 800 barg, about 50 barg to about 800 barg, 0 barg to about 700 barg, 1 barg to about 700 barg, about 5 barg to about 700 barg, about 10 barg to about 700 barg, 20 barg to about 700 barg, about 30 barg to about 700 barg, about 40 barg to about 700 barg, 50 barg to about 700 barg, about 60 barg to about 700 barg, about 70 barg to about 700 barg, about 80 barg to about 700 barg, about 90 barg to about 700 barg, about 100 barg to about 700 barg, about 200 barg to about 700 barg, about 300 barg to about 700 barg, about 400 barg to about 700 barg, about 50 barg to about 700 barg, 0 barg to about 600 barg, 1 barg to about 600 barg, about 5 barg to about 600 barg, about 10 barg to about 600 barg, 20 barg to about 600 barg, about 30 barg to about 600 barg, about 40 barg to about 600 barg, 50 barg to about 600 barg, about 60 barg to about 600 barg, about 70 barg to about 600 barg, about 80 barg to about 600 barg, about 90 barg to about 600 barg, about 100 barg to about 600 barg, about 200 barg to about 600 barg, about 300 barg to about 600 barg, about 400 barg to about 600 barg or about 50 barg to about 600 barg. In still another aspect, the pressure can range from about 1 barg to about 200 barg, about 5 barg to about 200 barg, about 10 barg to about 200 barg, about 20 barg to about 200 barg, about 30 barg to about 200 barg, about 40 barg to about 200 barg, about 50 barg to about 200 barg, 1 barg to about 100 barg, about 5 barg to about 100 barg, about 10 barg to about 100 barg, about 20 barg to about 100 barg, about 30 barg to about 100 barg, about 40 barg to about 100 barg, about 50 barg to about 100 barg, 1 barg to about 50 barg, about 5 barg to about 50 barg, about 10 barg to about 50 barg, about 20 barg to about 50 barg, about 30 barg to about 50 barg, or about 40 barg to about 50 barg.

The first reaction mixture flows through the one or more reaction vessels or reaction vessel train under the controlled temperature and controlled positive pressure of oxygen as described previously herein (namely, a controlled temperature of from about 5° C. to about 105° C. and a controlled positive pressure of oxygen from about 0 barg to about 1000 barg) for a period of time suitable to oxidize the organic compounds in the first reaction mixture to form a subsequent (or second) reaction mixture that comprises a mixture of organic acid products and nitrogen oxides (namely, $N_2O_3$, $N_2O_4$, NO, $NO_2$ and $N_2O$).

Once this subsequent (final) reaction mixture is formed, it is contacted with, delivered or recirculated to the vapor or headspace of one or more reaction vessels. If multiple reaction vessels are used, the subsequent (final) reaction mixture can be contacted, delivered or recirculated in any of the reaction vessels that contain the subsequent (final) reaction mixture. For example, recirculation may occur in the last or second to last reaction vessel comprising the reaction train.

The step of contacting, delivering or recirculating is important in the process of the present invention. Specifically, the contacting, delivery or recirculation step is used convert or recycle the nitrogen oxides contained in the subsequent (final) reaction mixture and gases back to nitric acid ($HNO_3$). This "converted" or "recycled" nitric acid can be reused in the oxidation process through methods described herein.

The contacting, delivering or recirculating can be conducted using any technique known in the art provided that a means is used that provides for a high surface area of contact between the gas and liquid phases contained in the subsequent final reaction mixture thereby allowing the nitrogen oxides to be converted or recycled back to nitric acid. The most important aspect is that some means is used to increase the surface area. Basically, any means for creating a high surface area of contact between the gas and liquid phases contained in a reaction vessel can be used in the process of the present invention. For example, the reaction vessel can comprise a pump at the bottom and a spray nozzle at the top. The pump transports the subsequent (final) reaction mixture to the top of the reaction vessel to one or more spray nozzles which spray the reaction mixture into the reaction vessel thereby creating a high surface area of contact. Alternatively, a falling film contactor or packed bed (such as a random, structured, or anything that can cause high surface area contact as known by those skilled in the art), where liquid is pumped from the bottom to the top of a device that creates high surface area as the liquid drops through the tubes of a heat exchanger or a high surface area bed can be used. Alternatively, a high surface area of contact between the gas and liquid phases contained in the subsequent (final) reaction mixture can be created by employing an agitator which can be used to create a high rate of agitation (either horizontal or vertical) in one or more reaction vessels thereby resulting in the reaction mixture being thrown or pushed into the vapor space above the liquid. High rates of agitation using an agitator in one or more reaction vessels employed in the process of the present invention can be determined using routine techniques known to those skilled in the art.

While conducting an experiment to understand if improving the mass transfer between the gas and liquid phases the reaction would speed up the reaction, the inventors surprisingly discovered that the oxidation reaction rates did not increase and in fact, the oxidation was quenched and conversion of the organic substrate into organic acid products was stopped. Specifically, the inventors found that when the subsequent (final) reaction mixture was sprayed from one or more spray nozzles at the top of the reaction vessel during this contacting, delivering or recirculating step, that the oxidation reaction immediately terminated, which was immediately identified/recognized by reduced cooling load and the colors of the NOX gas and liquids changing from dark to clear relatively quickly. This surprising result may be used to control the energetic oxidation reaction, particularly in preventing over oxidation of the organic substrate once the desired level of oxidation has been reached. This is particularly effective when combined with improved nitric acid regeneration (discussed more in the next paragraph below) through cooling of the headspace which leads to faster oxidation rates and makes control over the degree of oxidation difficult to control.

Additionally, the inventors also discovered that the contacting, delivering or recirculating step allowed for the more efficient recovery of nitric acid as the nitric compounds were more quickly converted to nitric acid due to the efficient contact of the vapor and liquid. The inventors believe that the reason the reaction is terminated with this step is that the nitrogen oxides contained in both the headspace and the subsequent (final) reaction mixture are converted back to nitric acid. Once the contacting, delivering or recirculating (recirculation) step is completed and the nitrogen oxides converted to nitric acid, then the nitric acid can be recovered or removed from the subsequent (final) reaction mixture to give a final reaction mixture of organic acids that are suitable for further processing. The nitric acid can be recovered or removed from the subsequent reaction mixture using any technique known in the art. For example, evaporation, distillation, nanofiltration, diffusion dialysis or alcohol or ether precipitation can be used. Regardless of the technique used, a significant portion of the nitric acid is removed from the subsequent (final) reaction mixture. In one aspect, the term "significant" when used in connection with removal of nitric acid from the subsequent (final) reaction mixture means that at least 65% of the nitric acid is removed from the subsequent (final) reaction mixture. In another aspect, the term "significant" when used in connection with removal of nitric acid from the subsequent (final) reaction mixture means that at least 70% of the nitric acid is removed from the subsequent (final) reaction mixture. In still yet another aspect, the term "significant" when used in connection with removal of nitric acid from the subsequent (final) reaction mixture means that at least 75% of the nitric acid is removed from the subsequent (final) reaction mixture. In still yet another aspect, the term "significant" when used in connection with removal of nitric acid from the subsequent (final) reaction mixture means that at least 80% of the nitric acid is removed from the subsequent (final) reaction mixture. In another aspect, the term "significant" when used in connection with removal of nitric acid from the subsequent (final) reaction mixture means that at least 85% of the nitric acid is removed from the subsequent (final) reaction mixture. In another aspect, the term "significant" when used in connection with removal of nitric acid from the subsequent (final) reaction mixture means that at least 90% of the nitric acid is removed from the subsequent (final) reaction mixture. In another aspect, the term "significant" when used in connection with removal of nitric acid from the subsequent (final) reaction mixture means that at least 95% of the nitric acid is removed from the subsequent (final) reaction mixture. In another aspect, the term "significant" when used in connection with removal of nitric acid from the subsequent (final) reaction mixture means that at least 99% of the nitric acid is removed from the subsequent (final) reaction mixture. In another aspect, the term "significant" when used in connection with removal of nitric acid from the subsequent (final) reaction mixture means that 99.9% of the nitric acid is removed from the subsequent (final) reaction mixture. For example if the nitric acid is to be removed by evaporation, any evaporator known in the art can be used. Examples of evaporators that can be used in the process of the present invention include, but are not limited to, vertical-pipe, horizontal-pipe, slanting-pipe, rotor or thin-layer, centrifugal, worm and falling-film evaporators, tube-bundle evaporators, basket evaporators, high viscosity evaporators, evaporators with one or more scrubbers, evaporators with one or more boilers, evaporators with one or more distillation columns, evaporators with external return pipe and forced circulation, evaporators with external heating elements and forced circulation and other evaporators known to those skilled in the art. In one aspect, the method of evaporation comprises the use of at least one wiped film evaporator. In an alternative aspect, the method of evaporation comprises the use of at least two wiped film evaporators. In yet another aspect, the method of evaporation comprises the use of a wiped film evaporator and another type of evaporator such as a vertical-pipe evaporator, a horizontal-pipe evaporator, a basket evaporator, etc. In one aspect, more than one evaporator is used in the reaction train. In one aspect, more than two evaporators are used in the reaction train. In another aspect, more than three evaporators are used in the reaction train. In yet another aspect, more than four evaporators are used in the reaction train. In still another aspect, more than one evaporator is used in the reaction train in which at least one evaporator contains a scrubber, condenser or a distillation column. In still another aspect, more than two evaporators are used in the reaction train in which at least one evaporator contains a scrubber, condenser or a distillation column. In still another aspect, more than three evaporators are used in the reaction train in which at least one evaporator contains a scrubber, condenser or a distillation column. In still another aspect, more than four evaporators are used in the reaction train in which at least one evaporator contains a scrubber, condenser or a distillation column.

Alternatively, as mentioned previously, the nitric acid can be removed from the subsequent (final) reaction mixture using diffusion dialysis. Diffusion dialysis can be used to remove nitric acid from the reaction mixture instead of or in conjunction with an evaporator. This process is typically used for the separation of common inorganic acids such as hydrochloric acid, sulfuric acid, or nitric acid from multivalent metal cations such as $Cu^{2+}$ or $Zn^{2+}$. The aqueous acid feedstock of the inorganic acid and metal salt(s) and a separate water stream are routed through a diffusion dialysis system consisting of low pressure pumps and an appropriate membrane system. Two aqueous exit streams are generated, an acid recovery stream comprised primarily of inorganic acid with some metal salt(s), and a product recovery stream comprised of primarily metal salt(s) with some inorganic acid. The separate streams can be subjected to further diffusion dialysis as needed to give a stream with higher inorganic acid concentration and lower metal salt concentrations, and a stream with higher metal salt concentration and lower inorganic acid concentration. This separation technique was applied to nitric acid oxidation reaction mixtures as prepared by the described methods herein, and was found to perform in the same manner as used in separation of inorganic acids from metal salts. The bulk of the nitric acid with some organic acid products, was in the acid recovery stream, and the bulk of the organic acid products with some of the nitric acid, was in the organic product recovery stream. The use of this technology to separate nitric acid from the organic acid products produced from the oxidation process described here is a very low energy process, operates at ambient temperature, and can be run continuously. It offers an additional advantage over direct evaporation/distillation of nitric acid from the reaction mixture in that in the latter process, additional oxidative processes can occur generating additional nitrogen oxide gases that have to be contained, removed and/or converted to oxides of nitrogen that are convertible to nitric acid. In contrast, the diffusion dialysis process operates at dilute concentrations and the recovered nitric acid stream from the diffusion dialysis process is low in carbohydrate product content and evaporation/distillation of the recovered nitric acid is achieved with minimal oxidation and nitrogen oxide formation occurring during nitric acid recovery.

It is recognized that the final reaction mixture from which nitric acid has been removed may be made basic to convert any residual or remaining nitric acid to inorganic nitrate, and converting the organic acids to a mixture of organic acid salts. Neutralization to a pH greater than 7 with inorganic base, without removal of nitric acid, requires base for all of the nitric acid plus the organic acids and the nitric acid is not directly recovered for further use. In contrast, partial recovery of the nitric acid for reuse by vacuum distillation is advantageous because the recovered nitric acid can be used again for oxidation purposes, although it is difficult to remove all the residual nitric acid from the syrupy concentrate with ease.

Depending upon the starting organic compounds, the specific reaction conditions employed, and the target products, this solution can be treated accordingly to give the organic acids in one or more forms. Organic acids can be obtained in free acid forms, as disalts, mono salts, acid lactones, and/or dilactones, or as mixtures of various salt forms, and/or acid and/or acid lactone forms. Acids generated from oligosaccharides and other higher molecular weight carbohydrates are mixtures which can contain some of the above aldonic and aldaric acids plus higher molecular weight acids derived from higher molecular weight carbohydrates. These acids can be also be obtained in various acid, lactone and salt forms.

Additionally, when oxidation products are obtained from direct concentration of the reaction mixture that removes most of the nitric acid, or by subjecting the oxidation reaction mixture to diffusion dialysis followed by removal of the bulk of the remaining nitric acid by an evaporation/distillation step, residual nitric acid can be removed as nitrate and recovered by a membrane filtration method. When the resultant syrupy product/residual nitric acid mixture is treated with an inorganic base to a pH greater than 7, the resulting solution contains inorganic nitrate and the salt(s) of the product organic acids. This solution is then subjected to filtration, typically nanofiltration, with the bulk of inorganic nitrate passing through the membrane and into the permeate, and the bulk of the organic product remaining in the retentate. The prior art has reported removal of inorganic nitrate from organic acid salts after nitric acid oxidation using ion retardation chromatography (See, D. E. Kiely and G. Ponder, U.S. Pat. No. 6,049,004, Apr. 11, 2000). However, ion retardation chromatography is not as fast, not as applicable on a large scale, and not as efficient as the filtration methods described herein. In the oxidation processes of the current invention, the remaining retentate contains the organic acid salt forms with minimal inorganic salt content. The presence of only small amounts of inorganic nitrate in the organic acid salt products renders purification and/or isolation of the organic acid salt products or non-salt products greatly improved over previously reported methods.

In an alternative aspect, the current invention also comprises a mixture of one or more organic acids, produced by the oxidation methods described herein. The mixture of one or more organic acids may be the result of the oxidation of a variety of organic compounds. The mixture of one or more organic acids generally includes the oxidation products of monohydric alcohols, diols, polyols, aldehydes, ketones, carbohydrates, and mixtures thereof. Non-limiting examples of carbohydrates suitable for oxidation by the processes of the current invention include, but are not limited to, monosaccharides, such as the common monosaccharides D-glucose, D-mannose, D-xylose, L-arabinose, D-arabinose, D-galactose, D-arabinose, D-ribose, D-fructose; disaccharides, such as the common disaccharides maltose, sucrose, isomaltose, and lactose; oligosaccharides, for example, maltotriose and maltotetrose; aldonic acids such as D-gluconic acid, D-ribonic acid, and D-galactonic acid; glucoheptonic acid; aldonic acid esters, lactones and salts that include but are not limited to those derived from D-gluconic acid, D-ribonic acid, glucoheptonic acid, and D-galactonic acid; alduronic acids, for example, D-glucuronic acid and L-iduronic acid; alduronic esters, lactones and salts that include but are not limited to those derived from D-glucuronic acid and L-iduronic acid; alditols that include glycerol, threitol, erythritol, xylitol, D-glucitol; alditols with more than six carbon atoms; cyclitols, for example common cyclitols such as myo-inositol and scyllitol; corn syrups with different dextrose equivalent values; other aldonic acids and salts thereof, such as, glucoheptonic acids, glycerbionic acids, erythrobionic acids, threobionic acids, ribobionic acids, arabinobionic acids, xylobionic acids, lyxobionic acids, allobionic acids, altrobionic acids, glucobionic acids, mannobionic acids, gulobionic acids, idobionic acids, galactobionic acids, talobionic acids, alloheptobionic acids, altroheptobionic acids, glucoheptobionic acids, mannoheptobionic acids, guloheptobionic acids, idoheptobionic acids, galactoheptobionic acids and taloheptobionic acids; glycols such as ethylene glycol, diethylene glycols, triethylene glycols or mixtures thereof; mixtures of carbohydrates from different biomass, plant or microorganism sources; polysaccharides from biomass, plant or microorganism sources (such as starch or celluloses) and of varying structures, saccharide units and molecular weights.

Additionally, the mixture of one or more organic acids may include the acid or salt forms of the oxidized organic compound. Suitable examples of organic acid salts include, but are not limited to sodium hydrogen glucarate, potassium hydrogen glucarate, lithium hydrogen glucarate, disodium glucarate, sodium potassium glucarate, dipotassium glucarate, dilithium glucarate, lithium sodium glucarate, lithium potassium glucarate, zinc glucarate, calcium glucarate, sodium hydrogen xylarate, potassium hydrogen xylarate, lithium hydrogen xylarate, disodium xylarate, sodium potassium xylarate, dipotassium xylarate, dilithium xylarate, lithium sodium xylarate, lithium potassium xylarate, zinc xylarate, calcium xylarate, sodium gluconate, potassium gluconate, lithium gluconate, disodium gluconate, sodium potassium gluconate, dipotassium gluconate, dilithium gluconate, lithium sodium gluconate, lithium potassium gluconate, zinc gluconate, calcium gluconate, sodium galactarate, potassium galactarate, lithium galactarate, disodium galactarate, sodium potassium galactarate, dipotassium galactarate, dilithium galactarate, lithium sodium galactarate, lithium potassium galactarate, zinc galactarate, calcium galactarate, sodium hydrogen tartarate, potassium tartarate, lithium hydrogen tartarate, disodium tartarate, sodium potassium tartarate, dipotassium tartarate, dilithium tartarate, lithium sodium tartarate, lithium potassium tartarate, zinc tartarate, sodium hydrogen tartronate, potassium hydrogen tartronate, lithium hydrogen tartronate, disodium tartronate, sodium potassium tartronate, dipotassium tartronate, dilithium tartronate, lithium sodium tartronate, lithium potassium tartronate, zinc tartronate, calcium tartronate, sodium hydrogen oxalate, potassium hydrogen oxalate, lithium hydrogen oxalate, disodium oxalate, sodium potassium oxalate, dipotassium oxalate, dilithium oxalate, lithium sodium oxalate, lithium potassium oxalate, zinc oxalate, calcium oxalate, sodium glycolate, potassium glycolate, lithium glycolate, disodium glycolate, sodium potassium glycolate, dipotassium glycolate, dilithium glycolate, lithium sodium glycolate, lithium potassium glycolate, zinc glycolate, calcium glycolate, sodium glycerate, potassium glycerate, lithium glycerate, zinc glycerate, calcium glycerate, and combinations thereof. In another aspect, the hydroxycarboxylic acid may include, but is not limited to, disodium glucarate, sodium potassium glucarate, dipotassium glucarate, zinc glucarate, disodium xylarate, sodium potassium xylarate, dipotassium xylarate, zinc xylarate, disodium galactarate, sodium potassium galactarate, dipotassium galactarate, zinc galactarate, and combinations thereof.

EXAMPLES

Example 1

General Methods for High Surface Area Contact for Examples 2-3

Oxidations were carried out in a Metler Toledo Labmax reactor which is designed to operate under computer control. The Labmax was fitted with an overhead agitation motor that drove a stir shaft fitted with an anchor style agitation paddle. The reactor was made of glass and had a silicon oil filled jacket for cooling and heating. In addition, the Labmax was fitted with an overhead balance in communication with a metering pump for controlled dosing of reactants into the reactor, and resistance temperature detector ("RTD") temperature probes to measure the temperature of both the reactor contents and the reactor jacket oil. A Mettler Toledo LMPress 60 pressure controller was used to maintain oxygen pressure of 1.0 barg+/−0.04 barg within the reactor. A pressure manifold fitted with a pressure relief valve, a rupture disc, and a pressure gauge was added to the head of the reactor. The Labmax was controlled using iControlLabmax software version 4.0 which allows the user to specify reaction parameters, measures and logs data, and uses proportional integral derivative (PID) loop processing to maintain stable material temperatures during a reaction and dose reactants into the reactor at a given rate.

Example 2

Oxidation Quenching by Circulation, Comparison of Non-Circulated and Circulated Oxidations 411 g (4.5 moles) of concentrated nitric acid was added to the reactor and the iControl software was used to maintain a reaction temperature of 25° C. and an agitation speed of 200 RPM for the duration of the reaction. Immediately after the nitric acid was added 0.31 g (4.5 millimoles) of sodium nitrite was added to the reactor and the reactor was sealed and pressurized with 1 barg oxygen. 62.5% D-glucose solution was dosed into the reactor at a rate of 2.88 g/min until 432.4 g (1.5 moles) had been added (150 min) After a short induction period, the mixture began to react exothermically as indicated by the jacket temperature having to run at colder and colder temperatures to maintain the material temperature of 25° C. After 35 minutes, the jacket temperature was running at 4.5° C. to maintain a reaction temperature of 25° C. The headspace filled with dark brown $NO_2$ gas and the liquid mixture turned dark green. At this time, the reaction began to slowly subside taking about 6 hours for the jacket temperature to rise to 20° C. to maintain a reaction temperature of 25° C. The headspace continued to be filled with dark brown gasses and the liquid mixture continued to be dark green in color until the reaction was fully quenched/terminated by adding a liter of cold water to the reactor. The exothermicity, gas production, and green liquid color observations were shown to be typical of all nitric acid oxidations performed in a closed vessel under oxygen pressure regardless of molar ratio or batch size.

Next, an identical reaction was performed except this time at approximately 25 minutes into the oxidation, a recirculation pump was turned on and the material was sprayed into the headspace of the reactor at a rate of about 75 ml/min so that the material was removed from the bottom of the reactor and sprayed through the headspace of the reactor and back onto the liquid surface for the duration of the reaction Immediately, the reaction began consuming oxygen indicated by the LM Press 60 having to increase its oxygen flow rate to the reactor in order to maintain the 1 barg pressure, and the brown $NO_2$ gas in the headspace began to dissipate resulting in a colorless headspace and the emerald green color in the liquid lightened up. The increased consumption of oxygen is an indication that $NO_x$ species are being oxidized back to nitric acid because the oxidation not only consumes oxygen but also results in a net pressure loss which must be made up with more oxygen. Within a few minutes, the exothermicity of the oxidation was significantly reduced indicated by the jacket temperature running at 17° C. to maintain the same operating temperature (a 63% reduction in delta T between jacket and material temperatures when compared to the non-circulated batch at the same time point). The reduction in exothermicity was an indication that the oxidation rate was slowing down and the reaction was being quenched. The green color in the liquid began to fade to pale yellow over the course of 1 hour. The early consumption of oxygen, and the reduction in exothermicity, gas production, and green liquid color were all indications of the oxidation being quenched or slowed down by the recirculation.

Example 3

Circulated Oxidation 205.5 g (2.25 moles) of 69% nitric acid was added to the reactor and the iControl software was used to maintain a reaction temperature of 25° C. and an agitation speed of 200 RPM for the duration of the reaction. 0.46 g (6.7 millimoles) of sodium nitrite was added to the reactor and the reactor was sealed and pressurized with 1 barg oxygen. Then 62.5% D-glucose solution was dosed into the reactor at a rate of 2.88 g/min until 648.6 g (2.25 moles) had been added (225 min) After about 20 minutes, the mixture began to react exothermically and brown $NO_x$ gases began to fill the headspace of the reactor and the liquid contents of the reactor turned emerald green in color. At this time, a recirculation pump was turned on and the material was sprayed into the headspace of the reactor at a rate of about 75 ml/min so that the material was removed from the bottom of the reactor and sprayed through the headspace of the reactor and back onto the liquid surface for the duration of the reaction. Immediately, the reaction began consuming oxygen indicated by the LM Press 60 having to increase its oxygen flow rate to the reactor in order to maintain the 1 barg pressure, and the brown $NO_2$ gas in the headspace began to dissipate resulting in a colorless headspace. The increased consumption of oxygen is an indication that $NO_x$ species are being oxidized back to nitric acid because the oxidation not only consumes oxygen but also results in a net pressure loss which must be made up with more oxygen. Within a few minutes, The exothermicity of the oxidation was significantly reduced indicated by a 13° C. increase in jacket temperature to maintain the same operating temperature (an 86% reduction in delta T between the jacket temperature and the material temperature). The reduction in exothermicity was an indication that the oxidation rate was slowing down and the reaction was being quenched. The green color in the liquid began to fade to pale yellow over the course of 1 hour. The early consumption of oxygen, and the reduction in exothermicity, gas production, and reduction in green liquid color were all indications of the oxidation being quenched or slowed down by the recirculation.

Example 4

General Methods for Examples 5-6

Oxidations were carried out in a Metler Toledo Labmax reactor which is designed to operate under computer control. The Labmax was fitted with an overhead agitation motor that drove a stir shaft fitted with four propeller type agitation paddles spaced equally throughout the height of the reactor. The reactor was made of glass and had a siliconoil filled jacket for cooling and heating. In addition, the Labmax was fitted with an overhead balance in communication with a metering pump for controlled dosing of reactants into the reactor, and RTD temperature probes to measure the temperature of both the reactor contents and the reactor jacket oil and a type K thermocouple was used to measure the temperature of the headspace. A Mettler Toledo LMPress 60 with a pressure transducer and internal PID loop processing was used to maintain oxygen pressure of 1.0 barg+/−0.04 barg within the reactor. A pressure manifold fitted with a pressure relief valve, a rupture disc and a pressure gauge was added to the head of the reactor. The reactor was equipped with a stainless steel condenser coil that extended inside the reactor from the top to about half way down the reactor. This condenser coil could be used to cool the top portion of the reactor independently of the oil jacket. The Labmax was controlled using iControl Labmax software version 4.0 which allows the user to specify reaction parameters, measures and logs data, and uses PID loop processing to maintain stable material temperatures during a reaction and dose reactants into the reactor at a given rate. The headspace of the reactor was plumbed into an external FT-IR gas cell with valves allowing gas samples to be removed from the headspace of the reactor. The gas cell was fitted into a Thermo Scientific Antaris Industrial Gas System (IGS) which could be used to take FT-IR spectra of the gas samples in real time. All spectra were obtained using the average of 8 scans from 700-3900 wavenumbers (i.e., inverse centimeters) and a resolution of 0.5 wavenumbers. The IGS was calibrated using certified gas standards. The gas standards were diluted with nitrogen using an Environics 4040 Diluter which allows the user to flow standard gas and nitrogen through the cell at predetermined flow rates in order to achieve desired gas concentrations. A 10-point calibration curve was generated for each gas analyzed. Due to the equilibrium relationship of $NO_2$ and its dimer $N_2O_4$, the concentrations of both species are expressed in terms of total $NO_2$ units where total $NO_2$ units equals the concentration of $NO_2$ plus two times the concentration of $N_2O_4$.

Example 5

Oxidation of $NO_2$ to Nitric Acid by Headspace Cooling, Comparison of Headspace Cooling and no Headspace Cooling 1238.9 g (13.5 moles) of concentrated nitric acid was added to the reactor and the iControl software was used to maintain a reaction temperature of 25° C. for 3 hours and 25 minutes then increase to 30° C. for 45 min then increase again to 35° C. for 75 min. An agitation speed of 100 RPM was used for the duration of the reaction. 0.93 g (13.5 millimoles) of sodium nitrite was added to the reactor and the reactor was sealed and pressurized with 1 barg oxygen. 62.5% D-glucose solution was dosed into the reactor at a variable rate starting at 3.12 g/min and gradually increasing to 14.9 g/min until 1297.2 g (7.20 moles) had been added (205 min) After about 20 minutes, the mixture began to react exothermically as indicated by the jacket temperature needing to run at colder and colder temperatures to maintain the material temperature of 25° C. Gas samples were taken from the reactor every 20 minutes and analyzed with FT-IR for composition and quantification. After 25 minutes, brown $NO_x$ gasses began to fill the headspace of the reactor and the liquid contents of the reactor turned emerald green in color. After 4.5 hours, the total $NO_2$ units concentration had built to 70% in the headspace of the reactor then slowly decreased to about 59% at the end of the oxidation. Despite the liquid temperature being maintained at 25° C.-35° C., the temperature of the headspace slowly built to a maximum of 40° C. reaching this maximum at the same time the total $NO_2$ units concentration reached a max of 70%. This temperature build was due to the exothermic reaction $2\ NO+O_2 \approx 2\ NO_2$.

Then an identical oxidation was performed except this time the headspace condenser was activated and allowed to run at −12° C. for the duration of the experiment. After 25 minutes, brown $NO_x$ gasses began to fill the headspace of the reactor and the liquid contents of the reactor turned emerald green in color. After 4.5 hours the total $NO_2$ units concentration had built to 55% in the headspace of the reactor then slowly decreased to about 50% at the end of the oxidation. The headspace condenser was able to keep the temperature of the headspace below 20° C. despite the exothermic reaction $2\ NO+O_2 \approx 2\ NO_2$. This lower temperature shifts the equilibrium of the dimerization of $NO_2$ to $N_2O_4$ allowing for more $N_2O_4$ to form which then enables $N_2O_4$ to condense into the liquid phase. Once in the liquid phase the $N_2O_4$ reacts with water to make $HNO_3$ and $HNO_2$ according to the reaction $N_2O_4+H_2O \approx HNO_2+HNO_3$. The higher concentration of nitric acid in the liquid phase was indicated by the lower concentration of total $NO_2$ units in the gas phase. At the end of the oxidation, the jacket temperature of the reactor was adjusted so that the headspace could be cooled to 5° C. This resulted in the total $NO_2$ units concentration in the headspace gradually diminishing to 18% over a 60 min period allowing for more nitric acid recovery (a 74% reduction in $NO_2$ concentration compared to the non headspace cooled experiment).

Example 6

Oxidation of $NO_2$ to Nitric Acid by Headspace Cooling, Comparison of Headspace Cooling and no Headspace Cooling 1110 g (12.2 moles) of concentrated nitric acid was added to the reactor. Then 1.1 g (15.9 millimoles) of sodium nitrite and 1753 g of the above dextrose solution (6.1 moles) were added to the reactor and the iControl software was used to maintain a reaction temperature of 35° C. and an agitation speed of 300 RPM was used for the duration of the reaction. The reactor was then sealed and pressurized with 1 barg oxygen. After a short induction period, the mixture began to react exothermically as indicated by the jacket temperature needing to run at colder and colder temperatures to maintain the material temperature of 25° C. Gas samples were taken from the reactor periodically and analyzed with FT-IR for composition and quantification. After about 30 minutes, brown $NO_x$ gasses began to fill the headspace of the reactor and the liquid contents of the reactor turned emerald green in color. After 3.9 hours the total $NO_2$ units concentration had built to 57% in the headspace of the reactor then slowly decreased to about 46% at the end of the oxidation.

Then an identical oxidation was performed except in this experiment the headspace condenser was activated and allowed to run at −12° C. for the duration of the experiment. After about 30 minutes, brown $NO_x$ gasses began to fill the headspace of the reactor and the liquid contents of the reactor turned emerald green in color. After 3.9 hours the total $NO_2$ units concentration had built to 50.0% in the headspace of the reactor then slowly decreased to about 40% at the end of the oxidation. The headspace condenser was able to keep the temperature of the headspace below 20° C. despite the exothermic reaction $2\ NO+O_2 \approx 2\ NO_2$. This lower temperature shifts the equilibrium of the dimerization of $NO_2$ to $N_2O_4$ allowing for more $N_2O_4$ to form then enables $N_2O_4$ to condense into the liquid phase. Once in the liquid phase the $N_2O_4$ can react with water to make $HNO_3$ and $HNO_2$ according to the reaction $N_2O_4+H_2O \approx HNO_2+HNO_3$. The higher concentration of nitric acid in the liquid phase was indicated by the lower concentration of total $NO_2$ units in the gas phase. At the end of the oxidation, the jacket temperature of the reactor was adjusted so that the headspace could be cooled to −8° C. This resulted in the total NO₂ units concentration in the headspace gradually diminishing to 13% over a 60 min period allowing for more nitric acid recovery (a 77% decrease in total NO₂ units concentration compared to the no headspace cooling experiment).

Example 7

General Methods for Examples 8-11

Oxidations were carried out in a Metler Toledo Labmax reactor which is designed to operate under computer control. The Labmax was fitted with an overhead agitation motor that drove a stir shaft fitted with agitation paddles. Both glass and stainless steel reactors were used the reactors were equipped with silicon oil filled jackets for cooling and heating. In addition, the Labmax was fitted with an overhead balance in communication with a metering pump for controlled dosing of reactants into the reactor, and RTD temperature probes to measure the temperature of both the reactor contents and the reactor jacket oil and a type K thermocouple was used to measure the temperature of the headspace. A Mettler Toledo LMPress 60 with a pressure transducer and internal PID loop processing was used to maintain oxygen pressure within the reactor. A pressure manifold fitted with a pressure relief valve, a rupture disc and a pressure gauge was added to the head of the reactor. The Labmax was controlled using iControl Labmax software version 4.0 which allows the user to specify reaction parameters, measures and logs data, and uses PID loop processing to maintain stable material temperatures during a reaction and dose reactants into the reactor at a given rate. The headspace of the reactor was plumbed into an external FT-IR gas cell with valves allowing gas samples to be removed from the headspace of the reactor. The gas cell was fitted into a Thermo Scientific Antaris Industrial Gas System (IGS) which could be used to take FT-IR spectra of the gas samples in real time. All spectra were obtained using the average of 8 scans from 700-3900 wavenumbers (i.e., inverse centimeters) and a resolution of 0.5 wavenumbers. The IGS was calibrated using certified gas standards. The gas standards were diluted with nitrogen using an Environics 4040 Diluter which allows the user to flow standard gas and nitrogen through the cell at predetermined flow rates in order to achieve desired gas concentrations. A 10-point calibration curve was generated for each gas analyzed. Due to the equilibrium relationship of NO₂ and its dimer N₂O₄, the concentrations of both species are expressed in terms of total NO₂ units where total NO₂ units equals the concentration of NO₂ plus two times the concentration of N₂O₄.

Example 8

NO$_x$ Oxidation by Headspace Cooling. Comparison of Headspace Cooling vs. no Headspace Cooling Two side-by-side oxidations were performed for which all parameters were kept identical except for the use of headspace cooling. In both oxidations, 1.70 grams sodium nitrite was dissolved in 2,716 grams of 62.5% D-glucose solution then the mixture was loaded into a 7 liter stainless steel reactor. The reactor had separate cooling jackets and separate internal cooling coils for the top and bottom halves allowing for separate temperatures to be maintained in the gas and liquid phases of the reactor. The gas and liquid phases were agitated using an overhead stirring motor attached to an agitation shaft with one turbine impeller in the liquid phase and three impellers in the gas phase. The lower cooling system was used to maintain the glucose mixture at 20° C. 1,720 grams of 69% nitric acid was added to the mixture, the reactor was purged to reach a minimal amount of atmospheric gases and then pressurized with 4 barg of oxygen. For the headspace cooling experiment, the upper cooling system was adjusted to provide a surface temperature of −12° C. in the gas phase of the reactor and for the non-headspace cooled experiment no temperature control was used for the top half of the reactor. The mixture was allowed to react for 5.5 hours continually adjusting the lower cooling system temperature to maintain a material temperature of 36° C. in the aqueous portion of the reactor as the exothermic oxidation proceeded. A flow through gas cell was used to deliver headspace gasses from the reactor to the light path of an FT-IR spectrometer allowing for in situ measurements of headspace composition. After about 4.5 hours the headspace in the non-cooled experiment consisted of nearly 95% total NO₂ units and the reactor had to be vented to maintain 4 barg pressure. The headspace temperature rose to 50° C. in the non-cooled headspace due to the exothermic reaction 2 NO+O₂⇌2 NO2. At the same time point in the "headspace" cooled experiment (−12° C.), the headspace consisted of only 55% total NO₂ units (See, FIG. 1) and the reactor did not need to be vented to maintain 4 barg pressure. The headspace condenser was able to keep the temperature of the headspace below 5.5° C. despite the exothermic reaction 2 NO+O₂≈2 NO₂. This lower temperature shifts the equilibrium of the dimerization of NO₂ to N₂O₄ allowing for more N₂O₄ to form then enables N₂O₄ to condense into the liquid phase. Once in the liquid phase the N₂O₄ can react with water to make HNO₃ and HNO₂ according to the reaction N₂O₄+H₂O≈HNO₂+HNO₃.

Example 9

NO$_x$ Oxidation by Increased Agitation 1.1 grams sodium nitrite were dissolved in 1753 grams of 62.5% D-glucose solution then the mixture was loaded into a 6 liter glass reactor. The reactor contained a cooling jacket that was used to maintain the glucose mixture at 15° C. 1,110 grams of 69% nitric acid was added to the mixture and the reactor was pressurized with 1 barg of oxygen. The mixture was then allowed to react for 6 hours continually adjusting the jacket temperature to maintain a material temperature of 35° C. in the reactor as the exothermic oxidation proceeded. The reaction was agitated using an overhead stir motor attached to an agitation shaft with a paddle type agitator in the liquid space of the reactor, the motor was run at 300 RPM. A flow through gas cell was used to deliver headspace gasses from the reactor to the light path of an FT-IR spectrometer allowing for in situ measurements of headspace composition. During the course of the 7 hour oxidation the composition of NO₂ in the headspace reached a maximum of 56% then slowly diminished to a about 46% as the reaction subsided. The liquid material turned dark green in color indicating the presence of dissolved nitrogen oxide species and the headspace had turned dark brown in color due to the high concentration of NO₂ gas. At this time the jacket was used to cool the material to 7° C. and the agitation was increased to 475 RPM and the material was maintained at these conditions for an additional 17 hours. The decreased temperature effectively quenched the oxidation, which ceased the production of any new NO$_x$ species, and the increased agitation resulted in a larger surface area at the gas-liquid boundary which drove the equilibria of headspace chemistries allowing for effective oxidation of NO$_x$ back to HNO₃. At the end of the 17 hours, the readspace composition was again measured using the flow through FT-IR cell and the total $NO_2$ composition was found to be less than 0.25% and both the liquid and the headspace were colorless.

Example 10

$NO_x$ Oxidation by Circulation 1.70 grams sodium nitrite were dissolved in 2,716 grams of 62.5% D-glucose solution and the resulting mixture was loaded into a 7 liter stainless steel reactor. The reactor had separate cooling jackets and separate internal cooling coils for the top and bottom halves allowing for separate temperature zones in the headspace and the aqueous space of the reactor. The headspace and aqueous space were agitated using an overhead stirring motor attached to an agitation shaft with 1 impeller in the aqueous space and three impellers in the headspace. The lower cooling system was used to maintain the glucose mixture at 20° C. 1,720 grams of 69% nitric acid was added to the mixture, the reactor was pressurized with 4 barg of oxygen, and the upper cooling system was adjusted to provide a surface temperature of −12° C. in the headspace portion of the reactor. The mixture was allowed to react for 6 hours continually adjusting the lower cooling system temperature to maintain a material temperature of 36° C. in the aqueous portion of the reactor as the exothermic oxidation proceeded. After about 45 minutes, the aqueous material turned from a colorless solution to a dark green solution indicating the presence of dissolved $NO_2$ and aqueous $N_2O_3$ in the mixture. As the nitric acid was reduced to nitric oxide gas, the nitric oxide quickly reacted with the oxygen in the headspace and produced brown $NO_2$ gas. A flow through gas cell was used to deliver headspace gasses from the reactor to the light path of an FT-IR spectrometer allowing for in situ measurements of headspace composition. After the completion of the 6 hour oxidation period 334 mmoles of NO2 were measured in the headspace portion of the reactor. A sample of the liquid material was taken and analyzed for composition using Ion chromatography and mass spectrometry. These methods indicated the existence of 2.62 moles of nitrous acid and 969.2 moles of nitric acid in the mixture. Then the lower cooling system was used to reduce the temperature of the material in the aqueous space of the reactor to 20° C. effectively quenching the oxidation reaction and ceasing the production of any new $NO_x$ species. A recirculation pump was turned on and the liquid material was sprayed into the headspace of the reactor at a rate of 1 liter per minute. The use of a recirculating spray increased the surface area between the liquid and gas phases removing the mass transfer limitations resulting in a dramatic reduction in both $NO_2$ in the reactor headspace and $N_2O_3$ in the reactor liquid space. This resulted in both the liquid and the gas phases returning to a (normal) colorless state. After the recirculation period, the flow through FT-IR cell was used to measure 137 mmoles of $NO_2$ in the reactor headspace (a 59% decrease in $NO_2$). Another liquid sample was taken and the ion chromatography and mass spectrometry analysis of this sample indicated the existence of 0.57 moles of nitrous acid (a 78.4% decrease) and 21.30 moles of nitric acid (a 36.2% increase).

Example 11

NOx Oxidation by Circulation, Quantification of Dissolved NOx Species 1.1 grams sodium nitrite were dissolved in 1,753 grams of 62.5% D-glucose solution then the mixture was loaded into a 6 liter glass reactor. The reactor had a cooling jacket that could be used to maintain a constant material temperature inside the reactor during an exothermic reaction. This jacket was used to maintain the glucose mixture at 35° C. 1,110 grams of 69% nitric acid was added to the mixture, the reactor was pressurized with 1 barg of oxygen, and the mixture was allowed to react for 6 hours continually adjusting the jacket temperature to maintain a material temperature of 35° C. in the reactor as the exothermic oxidation proceeded. The reaction was kept well mixed using an overhead stir motor attached to an agitation shaft with a paddle type agitator in the liquid space of the reactor. The headspace of the reactor was cooled using a cooling coil with recirculating ethylene glycol chilled to −5° C. A flow through gas cell was used to deliver headspace gasses from the reactor to the light path of an FT-IR spectrometer allowing for in situ measurements of headspace composition. During the course of the 7 hour oxidation $NO_2$ began to build in the headspace of the reactor turning the headspace brown in color. The liquid material had turned dark green in color indicating the presence of dissolved nitrogen oxide species and the headspace had turned dark brown in color due to the high concentration of $NO_2$ gas. At this time the gas from the reactor was vented and the amount of dissolved nitrogen oxide species was quantified as follows.

The dark green material was transferred to a suitable vacuum vessel and de-gassed under reduced pressure with agitation. The outlet of the vacuum pump was attached to a flow meter and a flow through FT-IR cell so that both the flow rate and the composition of the gas removed from the liquid material could be measured. After about 10 minutes, the dark green liquid material had turned colorless and no more gas was being removed from the liquid as indicated by the flow meter reading zero. The loss of color was due to the disassociation of green $N_2O_3$ (l) to form one mole each of $NO_2$ (g) and NO (g). The data obtained from the flow meter and the FT-IR analysis was used to calculate the number of moles of $NO_2$ equivalents that was dissolved in the liquid with the following formula:

$$n = \sum \frac{1 \text{ atm} * F_i}{R * 20 \text{ sk}}$$

where n is number of moles, $F_i$ is the flow rate for the $i^{th}$ measurement in $cm^3$, 293 K is the average temperature in kelvin and R is the ideal gas constant 82.05 $cm^3$/min atm $K^{-1}$ $mole^{-1}$. Each of $N_2O_3$ and $N_2O_4$ were treated as two $NO_2$ equivalents while each of $NO_2$ and NO were treated as one $NO_2$ equivalent in this analysis. Using this method, approximately 1395 mmoles of $NO_2$ equivalents were measured.

Next, an identical oxidation was performed except this time at the end of the 7 hour oxidation the material was cooled to 8.5° C. effectively quenching the oxidation and ceasing the production of any new NOx species. Simultaneously, a recirculation pump was turned on and the liquid material was sprayed into the headspace of the reactor at a rate of 2 liters per minute. The use of a recirculating spray increased the surface area between the liquid and gas phases facilitating the oxidation of $NO_x$ to nitric acid resulting in a dramatic reduction in both $NO_2$ in the reactor headspace and dissolved $NO_x$ in the liquid space. The material was circulated in this manner for 90 min after which the same method was used to quantify the amount of dissolved $NO_2$ equivalents in the liquid. This time only 84 mmoles of dissolved $NO_2$ equivalents were measured (a 94% reduction from the non-circulated oxidation).

It is understood that the foregoing examples are merely illustrative of the present invention. Certain modifications of the articles and/or methods may be made and still achieve the objectives of the invention. Such modifications are contemplated as within the scope of the claimed invention.

What is claimed is:

1. A method of synthesizing a mixture of organic acids, the method comprising the steps of:
   (a) combining, over time, in one or more closed reaction vessels, under a positive pressure of oxygen and with continuous mixing, an organic compound and an aqueous solution of nitric acid to form a first reaction mixture, wherein the organic compound and the aqueous solution of nitric acid are introduced into the one or more closed reaction vessels;
   (b) flowing said first reaction mixture through the one or more closed reaction vessels while maintaining (i) a controlled temperature of from about 5° C. to about 105° C. in a portion of the reaction vessel, (ii) a reaction vessel headspace temperature of from about 80° C. to about −42° C., and (iii) a controlled positive pressure of oxygen of from about 0 barg to about 1000 barg, to form a subsequent reaction mixture comprising a mixture of organic acid products and nitrogen oxides, wherein the reaction vessel headspace is maintained at a lower temperature than the temperature of the liquid phase;
   (c) recirculating the subsequent reaction mixture to the reaction vessel vapor space headspace until the nitric acid oxidation is quenched; and
   (d) recovering nitric acid from the subsequent reaction mixture,
   wherein the organic compound is selected from the group consisting of monohydric alcohols, diols, polyols, aldehydes, ketones, carbohydrates, hydroxyacids, cellulose, starch and combinations thereof.

2. The method of claim 1, wherein the one or more closed reaction vessels comprises one or more reactors.

3. The method of claim 2, wherein the one or more closed reaction vessels are in series (continuous) or in parallel with one another (batch).

4. The method of claim 2, wherein the reactor is a continuously stirred tank reactor (CSTRs) or a tubular type plug flow reactor.

5. The method of claim 1, wherein the method is a continuous process.

6. The method of claim 1, wherein the method is a batch process.

7. The method of claim 1, wherein the organic compound comprises a single organic material or a mixture of organic materials.

8. The method of claim 1, further comprising the step of removing a significant portion of the nitric acid from the subsequent reaction mixture.

9. The method of claim 8, wherein the removal of the nitric acid is accomplished by an evaporation, distillation, nanofiltration, diffusion dialysis or alcohol or ether precipitation.

10. The method of claim 8, further comprising the step of making basic the subsequent reaction mixture from which most of the nitric acid has been removed to convert residual nitric acid to inorganic nitrate and the mixture of organic acids to a mixture of organic acid salts.

11. The method of claim 1, wherein the carbohydrates are selected from the group consisting of monosaccharides, disaccharides, oligosaccharides, aldonic acids, aldonic acid esters, aldonic acid salts, aluronic acids, alduronic acid esters, alduronic acid salts, alditols, cyclitols, corn syrups with different dextrose equivalent values, and monosaccharides, disaccharides, oligosaccharides and polysaccharides derived from plants, microorganisms or biomass sources.

12. The method of claim 1, wherein the nitrogen oxides are $N_2O_3$, $N_2O_4$, $NO$, $NO_2$ and $N_2O$.

* * * * *